US011786555B2

(12) United States Patent
Chandraratna et al.

(10) Patent No.: US 11,786,555 B2
(45) Date of Patent: *Oct. 17, 2023

(54) RAR SELECTIVE AGONISTS IN COMBINATION WITH IMMUNE MODULATORS FOR CANCER IMMUNOTHERAPY

(71) Applicant: IO THERAPEUTICS, INC., Houston, TX (US)

(72) Inventors: Roshantha A. Chandraratna, San Juan Capistrano, CA (US); Martin E. Sanders, Seattle, WA (US)

(73) Assignee: Io Therapeutics, Inc., Spring, TX (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/123,577

(22) Filed: Dec. 16, 2020

(65) Prior Publication Data

US 2021/0100844 A1 Apr. 8, 2021

Related U.S. Application Data

(63) Continuation of application No. 16/711,627, filed on Dec. 12, 2019, now Pat. No. 10,874,694, which is a continuation of application No. 16/519,544, filed on Jul. 23, 2019, now Pat. No. 10,532,074, and a continuation of application No. 16/452,800, filed on Jun. 26, 2019, now Pat. No. 10,532,073, which is a continuation of application No. 16/117,372, filed on Aug. 30, 2018, now Pat. No. 10,363,272, said application No. 16/519,544 is a continuation of application No. 16/117,372, filed on Aug. 30, 2018, now Pat. No. 10,363,272.

(60) Provisional application No. 62/552,814, filed on Aug. 31, 2017.

(51) Int. Cl.
| | |
|---|---|
| A61K 39/00 | (2006.01) |
| A61K 35/17 | (2015.01) |
| A61P 35/02 | (2006.01) |
| A61K 31/4965 | (2006.01) |
| A61K 31/167 | (2006.01) |
| A61K 35/15 | (2015.01) |
| A61K 31/69 | (2006.01) |

(52) U.S. Cl.
CPC .......... A61K 35/17 (2013.01); A61K 31/167 (2013.01); A61K 31/4965 (2013.01); A61K 35/15 (2013.01); A61P 35/02 (2018.01); A61K 31/69 (2013.01); A61K 2300/00 (2013.01)

(58) Field of Classification Search
CPC .. A61K 31/167; A61K 31/4965; A61K 35/15; A61K 2300/00; A61P 35/00
See application file for complete search history.

(56) References Cited

U.S. PATENT DOCUMENTS

| | | | |
|---|---|---|---|
| 4,326,055 A | 4/1982 | Loeliger | |
| 4,362,892 A | 12/1982 | Hindley | |
| 5,234,926 A | 8/1993 | Chandraratna | |
| 5,324,840 A | 6/1994 | Chandraratna | |
| 5,612,356 A | 3/1997 | Koshimura et al. | |
| 5,723,666 A | 3/1998 | Vuligonda et al. | |
| 5,739,338 A | 4/1998 | Beard et al. | |
| 5,776,699 A | 7/1998 | Klein et al. | |
| 5,824,685 A | 10/1998 | Campochiaro et al. | |
| 5,877,207 A | 3/1999 | Klein et al. | |
| 5,919,970 A | 7/1999 | Song et al. | |
| 5,958,954 A | 9/1999 | Klein et al. | |
| 5,965,606 A * | 10/1999 | Teng ...................... A61P 35/00 |
| | | | 514/456 |
| 6,037,488 A | 3/2000 | Song et al. | |
| 6,225,494 B1 | 5/2001 | Song et al. | |
| 6,387,950 B2 | 5/2002 | Nehme et al. | |
| 6,452,032 B1 | 9/2002 | Beard et al. | |
| 6,455,701 B1 | 9/2002 | Song et al. | |
| 6,534,544 B1 | 3/2003 | Teng et al. | |
| 6,653,322 B1 | 11/2003 | Chambon et al. | |
| 6,942,980 B1 | 9/2005 | Klein | |
| 7,476,673 B2 | 1/2009 | Tsang | |
| 9,907,768 B2 | 3/2018 | Chandraratna et al. | |
| 10,004,708 B2 | 6/2018 | Chandraratna | |
| 10,004,709 B2 | 6/2018 | Chandraratna | |
| 10,213,401 B2 | 2/2019 | Chandraratna et al. | |
| 10,231,944 B2 | 3/2019 | Chandraratna et al. | |
| 10,363,272 B2 | 7/2019 | Chandraratna et al. | |
| 10,471,030 B2 | 11/2019 | Chandraratna et al. | |
| 10,485,775 B2 | 11/2019 | Chandraratna et al. | |
| 10,532,073 B2 | 1/2020 | Chandraratna et al. | |
| 10,532,074 B2 | 1/2020 | Chandraratna et al. | |

(Continued)

FOREIGN PATENT DOCUMENTS

| | | |
|---|---|---|
| CA | 2974066 | 6/2016 |
| EP | 0661259 | 7/1995 |

(Continued)

OTHER PUBLICATIONS

Elias et al., Retinoic acid inhibits Th17 polarization and enhances FoxP3 expression through a Stat-3/Stat-5 independent signaling pathway. Blood, 111:1013-1020 (2008).
Dzhagalov et al., Regulation of CD8+ T lymphocyte effector function and macrophage inflammatory cytokine production by retinoic acid receptor gamma. The Journal of Immunology, 178:2113-2121 (2007).
Dzhagalov et al., Regulation of CD8+ T cell functions by RAR-gamma. Semin Immunol., 21(1):2-7 (2009).

(Continued)

*Primary Examiner* — Sheela J. Huff
(74) *Attorney, Agent, or Firm* — K&L Gates LLP; Louis C. Cullman; Michelle Glasky Bergman

(57) ABSTRACT

Disclosed herein are methods for treating cancer comprising administering CAR-modified immune cells and at least one Retinoic Acid Receptor agonist.

17 Claims, 13 Drawing Sheets

(56) References Cited

U.S. PATENT DOCUMENTS

| | | | |
|---|---|---|---|
| 10,874,627 B2 * | 12/2020 | Chandraratna | A61K 31/505 |
| 10,874,694 B2 | 12/2020 | Chandraratna et al. | |
| 2001/0018456 A1 | 8/2001 | Fesus et al. | |
| 2005/0148590 A1 | 7/2005 | Tsang | |
| 2005/0259203 A1 | 11/2005 | Kimura | |
| 2007/0077652 A1 | 4/2007 | Peled et al. | |
| 2008/0300312 A1 | 12/2008 | Chandraratna | |
| 2009/0176862 A1 | 7/2009 | Chandraratna et al. | |
| 2009/0181988 A1 | 7/2009 | Welsh | |
| 2009/0203720 A1 | 8/2009 | Zhao | |
| 2009/0214560 A1 | 8/2009 | Min et al. | |
| 2011/0085970 A1 | 4/2011 | Terrett et al. | |
| 2011/0150892 A1 | 6/2011 | Thudium et al. | |
| 2012/0189617 A1 | 7/2012 | Takayanagi et al. | |
| 2014/0086909 A1 | 3/2014 | Lu | |
| 2014/0286973 A1 | 9/2014 | Powell, Jr. | |
| 2015/0259420 A1 | 9/2015 | Triebel et al. | |
| 2015/0290194 A1 | 10/2015 | Wang et al. | |
| 2016/0067336 A1 | 3/2016 | Fandi et al. | |
| 2016/0075783 A1 | 3/2016 | King et al. | |
| 2016/0108123 A1 | 4/2016 | Freeman et al. | |
| 2016/0215059 A1 | 7/2016 | Liu et al. | |
| 2016/0317654 A1 | 11/2016 | Noelle | |
| 2016/0368989 A1 | 12/2016 | Dijk et al. | |
| 2017/0081409 A1 | 3/2017 | Dijk et al. | |
| 2017/0136063 A1 | 5/2017 | Perez et al. | |
| 2017/0354623 A1 | 12/2017 | Chandraratna | |
| 2018/0133179 A1 | 5/2018 | Chandrartna et al. | |
| 2018/0133180 A1 | 5/2018 | Chandrartna et al. | |
| 2018/0133181 A1 | 5/2018 | Chandrartna et al. | |
| 2018/0133182 A1 | 5/2018 | Chandrartna et al. | |
| 2018/0133183 A1 | 5/2018 | Chandrartna et al. | |
| 2021/0113506 A1 | 4/2021 | Chandraratna et al. | |

FOREIGN PATENT DOCUMENTS

| | | |
|---|---|---|
| WO | 1997/013505 | 4/1997 |
| WO | 1998/08546 | 3/1998 |
| WO | 2001/007028 A2 | 2/2001 |
| WO | 2001/074759 | 10/2001 |
| WO | 2002/028810 A2 | 4/2002 |
| WO | 2007/041398 A2 | 4/2007 |
| WO | 2008/121570 | 10/2008 |
| WO | 2014/160627 | 10/2014 |
| WO | 2014/163684 A1 | 10/2014 |
| WO | 2015/092420 A1 | 6/2015 |
| WO | 2016/015095 A1 | 2/2016 |
| WO | 2016/144976 A1 | 9/2016 |
| WO | 2017/031367 | 2/2017 |
| WO | 2017/091762 | 6/2017 |
| WO | 2017/096017 | 6/2017 |
| WO | 2017/201200 A1 | 11/2017 |
| WO | 2017/214575 A1 | 12/2017 |
| WO | 2019/014468 | 1/2019 |
| WO | 2019/014492 A1 | 1/2019 |

OTHER PUBLICATIONS

Guo et al., A retinoic acid-rich tumor microenvironment provides clonal survival cues for tumor-specific CD8+ T cells. Cancer Research, 72(20): 5230-5239 (2012).
Maire et al., Retinoid Receptors and Therapeutic Applications of RAR/RXR Modulators, Curr. Top. Med. Chern. 12 (6):505-527 (2012).
Park and Pan, The role of nuclear receptors in regulation of Th17/Treg biology and its implications for diseases, Cell. Mol. Immunol. 12(5):533-542 (2015).
Pohl et al., Transcription of retinoic acid receptor genes in transgenic mice increases CDS T-cell subset. Molecular Biology Reports, 17:135-142 (1993).
Takeuchi and Nishikawa, Roles of regulatory T cells in cancer immunity, Int. Immunol. 28(8):401-409 (2016).
Johnson AT et al. "Synthesis and characterization of a highly potent and effective antagonist of retinoic acid receptors." J Med Chem 38:4764-4767 (1995).
Naidoo J et al. "Immune modulation for cancer therapy" Br. J. Cancer 111:2214-2219, 2014.
Hodi FS et al. "Improved survival with ipilimumab in patients with metastatic melanoma" NEJM 363:711-723, 2010.
Keir ME et al. "PD-1 and its ligands in tolerance and immunity" Ann Rev Immunol 26:677-704, 2008.
Topolian SL et al. "Safety, activity, and immune correlates of anti-PD-1 antibody in cancer" NEJM 366:2443-3454, 2012.
Holmgaard KB et al. :Indoleamine 2,3-dioxygenase is a critical resistance mechanism in antitumor T cell immunotherapy targeting CTLA-4 J Exp Med 210:1389-1402, 2013.
Munn DH et al. "Indoleamine 2,3-dioxygenase and tumor-induced tolerance" J Clin Invest 117:1147-1154, 2007.
Mucida D et al. Reciprocal TH17 and regulatory T cell differentiation mediated by retinoic acid Science 317:256-260, 2007.
Pino-Lagos K et al. "A retinoic acid-dependent checkpoint in the development of CD4+ T cell-mediated immunity" J Exp Med 208:1767-1775, 2011.
Nowak EC et al. "Treatment with retinoid X receptor agonist IRX4204 ameliorates experimental autoimmune encephalomyelitis" Am J Translational Res 8:1016-1026, 2016.
Curiel TJ et al. "Specific recruitment of regulatory T cells in ovarian carcinoma fosters immune privilege and predicts reduced survival." Nat Med 10:942-949, 2004.
Teng M et al. "Identification of highly potent retinoic acid receptor alpha-selective antagonists" J Med Chem 40:2445-2451, 1997.
International Search Report and Written Opinion for International Application No. PCT/US2017/036870 dated Sep. 6, 2017.
Jones, PH, et al., "A phase I study of tazarotene in adults with advanced cancer" British Journal of Cancer 89:808-815 (2003).
Gargett et al., GD2-specific CAR T cells undergo potent activation and deletion following antigen encounter but can be protected from activation-induced cell death by PD-1 blockade. Molecular Therapy, vol. 24, No. 6, pp. 1135-1149 (2016).
Ghiaur et al., Regulation of human hematopoietic stem cell self-renewal by the microenvironment's control of retinoic acid signaling. Proc Natl Acad Sci USA, 110(40):16121-16126 (2013).
Huf et al., The paradox of response and survival in cancer therapeutics. Blood, vol. 107, No. 2, pp. 431-434 (2006).
Beard et al., Synthesis and biological activity of retinoic acid receptor-alpha specific amides. Bioorganic and Medicinal Chemistry Letters, vol. 12, pp. 3145-3148 (2002).
Johnson et al., Synthesis and biological activity of high-affinity retinoic acid receptor antagonists. Bioorganic & Medicinal Chemistry 7:1321-1338 (1999).
Kane et al., HPLC/UV quantitation of retinal, retinol, and retinyl esters in serum and tissues. Anal Biochem, 378 (1):71-79 (2008).
Oneru et al., A phase 1 clinical trial of adoptive T cell therapy using IL-12 secreting MUC-16ecto directed chimeric antigen receptors for recurrent ovarian cancer. Journal of Translational Medicine, 13:102 (2015).
Locke et al., Phase 1 results of ZUMA-1: A multicenter study of KTE-C19 anti-CD19 CAR T cell therapy in refractory aggressive lymphoma. Molecular Therapy, vol. 25, No. 1, pp. 285-295 (2017).
Long et al., Reduction of MDSCs with all-trans retinoic acid improves CAR therapy efficacy for sarcomas. Cancer Immunol Res, 4(10):869-880 (2016).
Makita et al., Clinical development of anti-CD19 chimeric antigen receptor T-cell therapy for B-cell non-Hodgkin lymphoma. Cancer Sci, 108:1109-1118 (2017).
M,S., Bone marrow (BM) stromal expression of cytochrome P450 (CYP) enzymes protects acute myeloid leukemia (AML) from all-trans retinoic acid (ATRA). Blood, 122: p. 1449a (2013).
Su et al., All-trans retinoic acid acitivity in acute myeloid leukemia: Role of cytochrome P450 enzyme expression by the microenvironment. PLOS One, 14pp (2015).
Tobita et al., Treatment with a new synthetic retinoid, Am80, of acute promyelocytic leukemia relapsed from a complete remission induced by all-trans retinoic acid. Blood, 90(3): 967-973 (1997).

(56) References Cited

OTHER PUBLICATIONS

Verfaille et al., Oral R115866 in the treatment of moderate to severe plaque-type psoriasis. J Eur Acad Dermatol Venereol, 21 (8):1038-1046 (2007).
Yoshida et al., All-trans retinoic acid enhances cytotoxic effect of T cells with an anti-CD38 chimeric antigen receptor in acute myeloid leukemia. Clinical & Translational Immunology, 5, e116 (2016).
Jetson et al., Practical synthesis of a chromene analog for use as a retinoic acid receptor alpha antagonist lead compound. European Journal of Medicinial Chemistry, vol. 63, pp. 104-108 (2013).
International Search Report and Written Opinion for PCT/US2018/048876; dated Dec. 11, 2018.
Mihara et al., All-trans retinoic acid and interferon-alpha increase CD38 expresion on adult T cell leukemia cells and sensitize them to T cells bearing anti-CD38 chimeric antigen receptors. Blood Cancer Journal, 6, e. 421 (2016).
Invitation to pay additional fees in PCT/US2018/048876; Oct. 9, 2018.
Porter et al., Chimeric Antigen Receptor-Modified T Cells in Chronic Lymphoid Leukemia, New England Journal of Medicine 365(8): 1-12, 2011.
Davila et al., CD-19-Targeted CAR T Cells as Novel Cancer Immunotherapy for Relapsed or Refractory B Cell Acute Lymphoblastic Leukemia, Clinical Advances in Hematology & Oncology 14(10):1-11, 2016.
Davila et al., CAR Therapy for CLL: What are the Challenges?, Hematology/Oncology Clinics of North America 27 (3):1-16, 2013.
Brudno et al., Toxicities of chimeric antigen receptor T cells: recognition and management, Blood 127(26):3321-3330, 2016.
Toma et al., RARalpha Antagonist RO 41-5253 Inhibits Proliferation and Induces Apoptosis in Breast Cancer Cells Lines, International Journal of Caner 78:86-94, 1998.
Szondy et al., Induction of Apoptosis by Retinoids and Retinoic Acid Repector Gamma-Selective compound in Mouse Thymocytes through a Novel Apoptosis Pathway, Molecular Pharmacology 51:972-982, 1997.
Johnson et al., Retinoid X Receptor (RXR) Agonist-Induced Activation of the Dominant-Negative RAR-Retinoic Acid Receptor alpha403 Heterodimers is Developmentally Regulated during Myeloid Differentiation, Molecular and Cellular Biology, 19(5):3372-3382, 1999.
National Center for Biotechnology Information. PubChem Compound Database; CID=24785198.
International Search Report and Written Opinion for PCT/US2018/041862; dated Oct. 15, 2018.
Alonso et al., Hedgehog and retinoid signaling alters multiple myeloma microenvironment and generates bortezomib resistance, J. Clin. Invent. 126(12):4460-4468, 2016.
Sharpe & Mount, Genetically modified T cells in cancer therapy:opportunities and challenges, Dis. Model Mech. 8 (4):337-350, 2015.
International Search Report and Written Opinion for PCT/US2018/041892; dated Sep. 20, 2018.
Thacher et al., Therapeutic applications for ligands of retinoid receptors. Current Pharmaceutical Design, 6, 25-28 (2000).
Yoshida et al., All-trans retinoic acid and interferon-alpha increase CD38 expresion on adult T-cell leukemia cells and sensitize them to T cells bearing anti-CD38 chimeric antigen receptors. Blood Cancer J, vol. 6, Article No. e421, pp. 1-4 (2016).
Hallahan et al., BMP-s mediates retinoid-induced apoptosis in medulloblastoma cells through a paracrine effect. Nature Medicine, 9(8): 1033-1038 (2003).
History of Changes for Study: NCT0279708: Study of IRX5183 in relapsed and refractory acute myeloid leukemia and high risk myelodysplastic syndrome. http://clinicaltrials.gov/ct2/history/NCT027497082V_1=View#StudyPageTop (2016).
Chaudhary et al., Regulatory T cells in the tumor microenvironment and cancer progression: role and therapeutic targeting. Vaccines, vol. 4, No. 28, 25 pp. (2016).
Retinoids in Fitzpatrick's Dermatology in General Medicine, 8e [retrieved from internet on Apr. 14, 2022 by NZ Examiner]. Retrieved from <https://accessmedicine.mhmedical.com/content.aspx2bookid=392§ionid=41138965> (2012).
Singaporean Search Report and Written Opinion, dated May 24, 2021, for Singaporean Patent Application No. 11202001479R.
Lynn et al., Targeting of folate receptor beta on acute myeloid leukemia blasts with chimeric antigen receptor-expressing. T cells. Blood, 125(22):3466-3476 (2015).
Singaporean Search Report and Written Opinion, dated Feb. 13, 2023, for Singaporean Patent Application No. 11202001479R.

\* cited by examiner

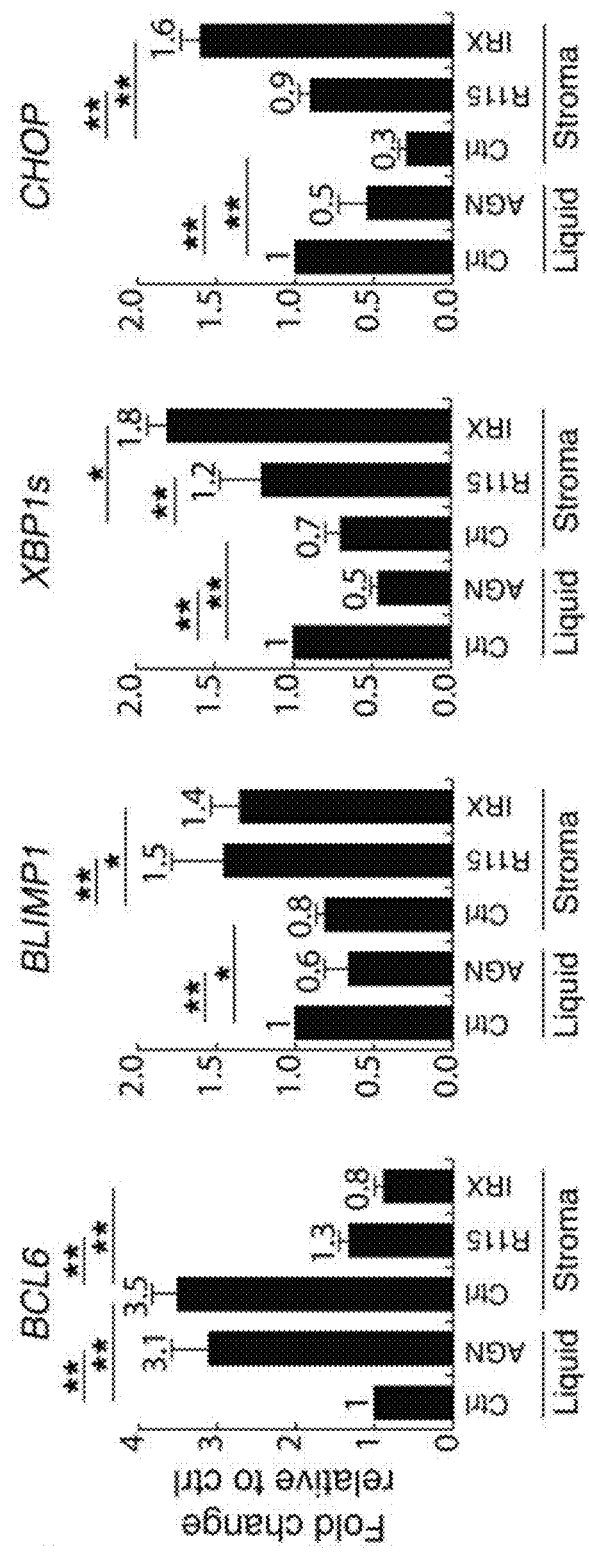

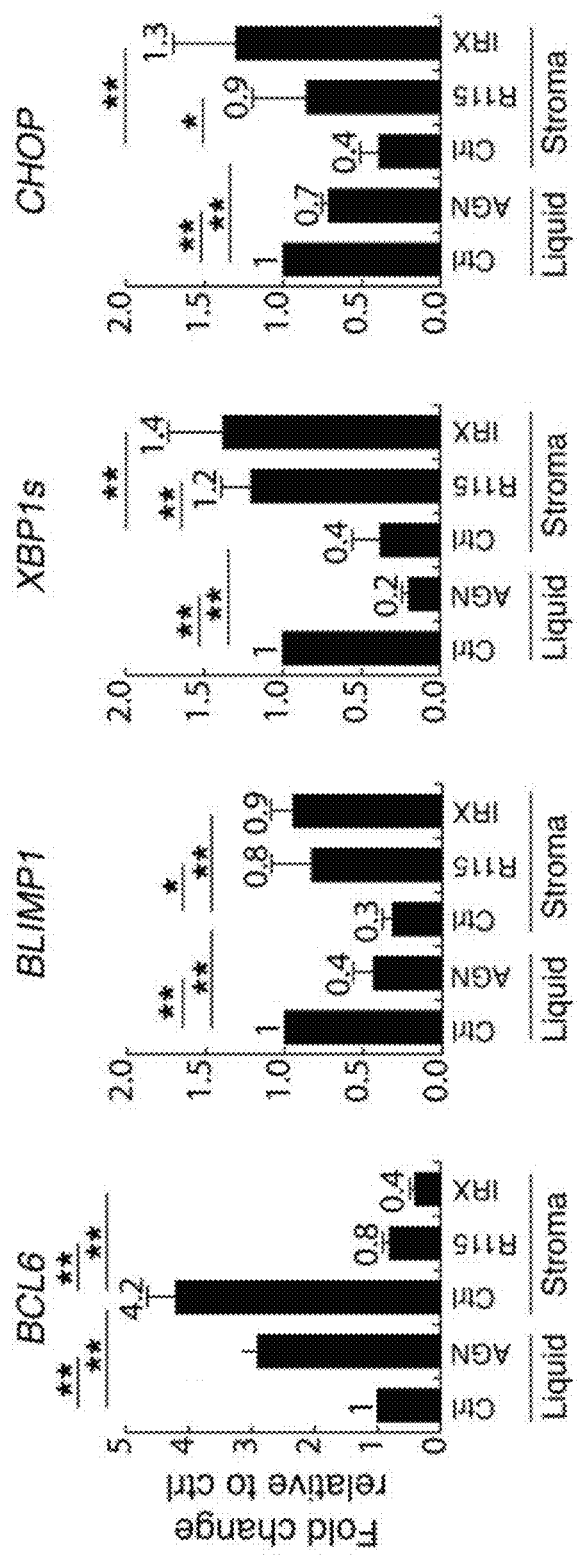

RAR SELECTIVE AGONISTS IN COMBINATION WITH IMMUNE MODULATORS FOR CANCER IMMUNOTHERAPY

RELATED APPLICATIONS

This application is a continuation of U.S. patent application Ser. No. 16/711,627, filed Dec. 12, 2019, now U.S. Pat. No. 10,874,694, which is a continuation of 1) U.S. patent application Ser. No. 16/452,800, filed Jun. 26, 2019, now U.S. Pat. No. 10,532,073, and 2) U.S. patent application Ser. No. 16/519,544, filed Jul. 23, 2019, now U.S. Pat. No. 10,532,074, each or which is a continuation of U.S. patent application Ser. No. 16/117,372, filed Aug. 30, 2018, now U.S. Pat. No. 10,363,272, which claims the benefit of U.S. Provisional Patent Application No. 62/552,814, filed on Aug. 31, 2017, the entire contents of which are each incorporated by reference herein.

BACKGROUND

For years, the cornerstones of cancer treatment have been surgery, chemotherapy, and radiation therapy. Over the last decade, targeted therapies—drugs that target cancer cells by homing in on specific molecular changes seen primarily in those cells—have also emerged as standard treatments for a number of cancers. A newer approach utilizing immunotherapy involves engineering immune cells to recognize and attack tumors.

Normal hematopoietic stem cells (HSCs) are primed to be highly sensitive to retinoids (compounds specific for the Retinoic Acid Receptor or RAR) but are maintained in a retinoid signaling-naïve state by isolating them from physiologic levels of retinoids. The bone marrow microenvironment, by expression of the enzyme CYP26 metabolically inactivates retinoic acid, regulates the exposure of the bone marrow to retinoids. This mechanism (CPY26-mediated retinoid metabolism) is dynamic and used by the bone marrow stroma to match HSC behavior to physiological needs. For example, steady state low levels of retinoids in the bone marrow niche maintains HSCs in a quiescent state, while during situations of stress (i.e., exposure to radiation or chemotherapy) higher retinoid levels are maintained to recruit HSCs into cell division and rescue hematopoiesis.

In subjects with hematologic malignancies, cancer HSCs are protected from retinoids by stromal CYP26, in a similar fashion to the normal situation. However, because of other alterations in the bone marrow niche in hematologic malignancies, such as differences in aldehyde dehydrogenase (ALDH) activity, there exists a therapeutic window for retinoids to be useful in the treatment of hematologic malignancies. Expression of CYP26 by the bone marrow microenvironment contributes to the protection of immature acute myeloid leukemia (AML) cells from all-trans retinoic acid (ATRA) and may explain why ATRA is not effective in treating AML. Exposure to pharmacological concentrations of ATRA, acting through retinoic acid receptor gamma (RARγ), induces CYP26 expression in the bone marrow microenvironment, thus protecting the cancer stem cells therein from retinoid activity. This mechanism also shields non-hematopoietic metastatic tumor cells in the bone marrow. However, the use of retinoid analogs which are not inactivated by CYP26 enables such retinoids to terminally differentiate, and thus eliminate, the cancer HSCs from the protective bone marrow niche. Since such differentiation is mediated by RARα and the use of RARα specific analogs, which are CYP26 resistant, enables the therapeutic differentiation-inducing activity without inactivation by the CYP26 enzyme.

Thus, the combination of RAR agonists, to induce differentiation of cancer stem cells, and targeted immunotherapy can be particularly useful in treating cancer.

SUMMARY

Disclosed herein are compounds for potentiation of targeted cancer immunotherapeutics. Compounds which act on retinoic acid receptors (RAR) are used in combination with chimeric antigen receptor (CAR)-modified immune cells (sometimes abbreviated as CAR-MIC) to potentiate the anti-cancer activity of the CAR-modified immune cells and/or immune checkpoint targeted therapeutics.

Retinoids and rexinoids have diverse activities. Particular retinoids have an anticancer effect based in terminally differentiating cancer stem cells. These differentiating retinoids, or differentiating RAR active agents, can be used in combination with CAR-MIC to increase the overall effectiveness of the immunotherapy. In some embodiments the differentiating retinoid is a RARα agonist. In some embodiments the RARα agonist is a RARα specific or selective agonist. In some embodiments the RARα agonists are CYP26 resistant (CYP26 metabolism-resistant retinoid means).

In some embodiments, the CAR-modified immune cells are, or comprise, CAR-modified T cells. In some embodiments, the CAR-modified immune cells are, or comprise, CAR-modified NK cells. In some embodiments, the CAR-modified immune cells are, or comprise, CAR-modified NKT cells. In some embodiments, the CAR-modified immune cells are, or comprise, CAR-modified macrophages. Further embodiments can comprise mixtures of these cell types. Most typically such cellular preparations are administered by infusion, for example intravenous infusion. In contrast, the RARα agonists are small molecules that can be administered orally, for example as pills or capsules and the like. Thus the RARα agonists and the CAR-modified immune cells may be administered on independent schedules.

In some embodiments, the RARα agonist is:

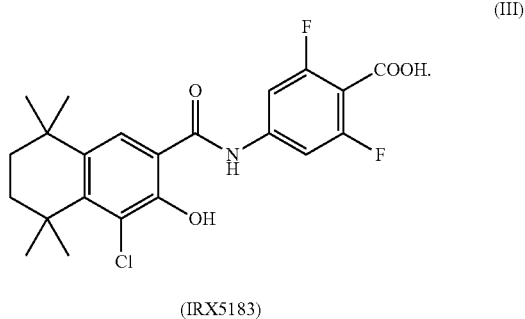

(III)

(IRX5183)

In other embodiments, the RARα agonist is tamibarotene (AM80), AM580, or Re 80.

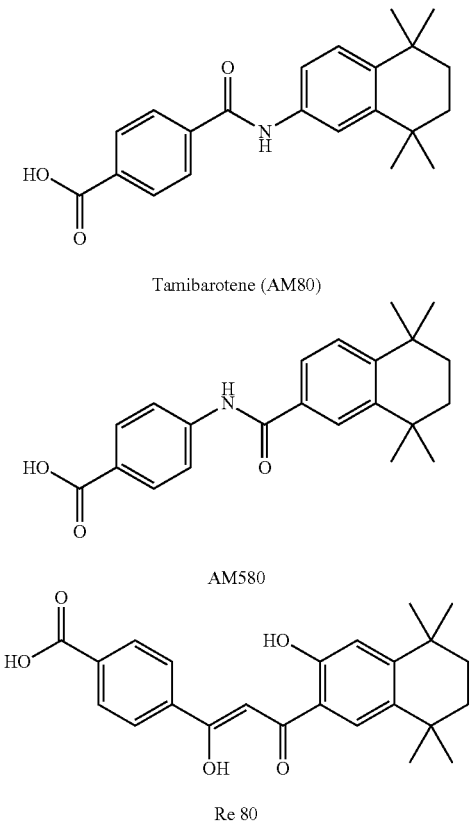

Tamibarotene (AM80)

AM580

Re 80

Other embodiments specifically exclude one or more of these RARα agonists.

In some embodiments, the cancer is a hematologic malignancy, such as acute myeloid leukemia or multiple myeloma. In some embodiments, the cancer is a solid tumor.

In some embodiments, the methods further comprise administering to the subject at least one immune checkpoint inhibitor. In some embodiments, the immune checkpoint inhibitor is an inhibitor of at least one of CTLA-4, PD-1, TIM-3, LAG-3, PD-L1 ligand, B7-H3, B7-H4, BTLA, or is an ICOS or OX40 agonist. In some embodiments, the immune checkpoint inhibitor is an antibody specific for at least one of CTLA-4, PD-1, TIM-3, LAG-3, PD-L1 ligand, B7-H3, B7-H4, BTLA, ICOS, or OX40. Other embodiments specifically exclude one or more of these agents.

In some embodiments, the methods comprise additionally administering at least one antineoplastic agent such as a cancer chemotherapy agent or targeted therapy agent. In some embodiments the antineoplasitc agent is bortezomib.

Also disclosed herein are methods of prolonging the disease-free survival of a cancer patient comprising, administering CAR-modified immune cells and at least one RARα agonist as compared to patients receiving CAR-modified immune cells but not receiving the RARα agonist. Other embodiments are methods of prolonging the progression-free survival or overall survival of a cancer patient comprising administering CAR-modified immune cells and at least one RARα agonist.

Also disclosed herein are methods of decreasing toxicity of CAR-modified immune cells comprising administering to a subject in need thereof at least one RARα agonist in combination with the CAR-modified immune cells such that as a result of the combination, a lower dose of CAR-modified immune cells is administered more safely and equally effectively than if the CAR-modified immune cells were administered alone; or that a higher dose of CAR-MIC can be administered with greater efficacy and equal safety.

Also disclosed herein are methods of treating cancer comprising administering to a subject in need thereof, chimeric antigen receptor (CAR)-modified immune cells, at least one RARα agonist, and at least one immune checkpoint inhibitor.

Also disclosed herein are methods of augmenting the production of CAR-modified immune cells by inclusion of an RARα agonist in the culture medium.

BRIEF DESCRIPTION OF THE DRAWINGS

FIG. 3A-H depicts the relative concentration of plasma markers BCL6 (FIG. 3A and E), BLIMP-1 (FIG. 3B and F), XBPS-1 (FIG. 3C and G), and CHOP (FIG. 3D and H) in multiple myeloma (MM) cell lines H929 (FIG. 3A-D) or CD138+ MM cells from three different patient samples (FIG. 3E-H) incubated for 5 days either in the absence of stroma (Liquid), with or without AGN (RA receptor antagonist AGN194310, 1 μM), or co-cultured with BM mesenchymal cells (Stroma), with or without R115 (CYP26 inhibitor R115866, 1 μM) or IRX (CYP26-resistant retinoid IRX5183, 1 μM). Expression in untreated liquid conditions was set at 1. Data are representative of 3 independent experiments with similar results and represent the mean ±SEM. *P≤0.05 and **P≤0.01, by repeated-measures 1-way ANOVA for determination of statistical significance between groups; P values were corrected for multiple comparisons using Dunnett's test. Ctrl, control; max, maximum.

(FIG. 12A) CFU experiments with NB4 cells treated with $10^{-7}$ M ATRA, IRX5183, or $10^{-8}$ M AM80; (FIG. 12B) OCI-AML3 cells and (FIG. 12C) Kasumi-1 cells treated with $10^{-6}$ M ATRA, IRX5183, or $10^{-7}$ M AM80 showed a decrease in clonogenic growth compared to control with AM80 and IRX5183 both off and on stroma. Data across three independent experiments.

DETAILED DESCRIPTION

Figure 1:
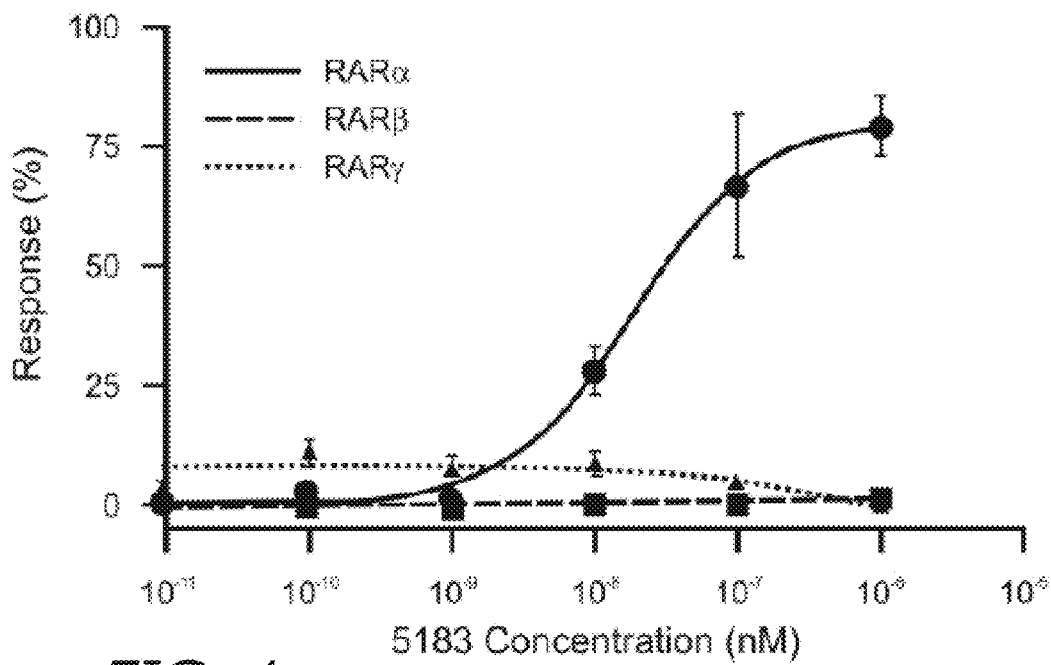
FIG. 1 depicts the extent to which compound IRX5183 binds to and activates transcription from RARα, RARβ, and RARγ using a transactivation assay.

Disclosed herein are combinations for therapy of cancer comprising coordinated administration of retinoid compounds and adoptive transfer of immune cells expressing chimeric antigen receptors (CAR-modified immune cells or CAR-MIC) and/or immune checkpoint targeted therapeutics. Compounds which act on retinoic acid receptors (RAR), in particular RARα agonists, can potentiate the activity of CAR-modified immune cells by causing cancer stem cells to differentiate and leave the bone marrow or tumor site and become available to be attacked by the CAR-modified immune cells.

By potentiation it is meant that the CAR-modified immune cells have greater and/or more rapid effect when a RARα selective agonist is used with the CAR-modified immune cells than when a RARα agonist is not used with the CAR-modified immune cells or, similarly, that a given degree of effect can be obtained with a smaller dosage of CAR-modified immune cells when the RARα agonist is also used than would be required if the RARα selective agonist were not used.

As used herein, the term "potentiate" refers to an improved efficacy of CAR-modified immune cells, or improved response by the patient, when used in combination with a RARα agonist compared to the use of CAR-modified immune cells in the absence of RARα agonist. As used herein, the term "augment" also refers to an improved effect when using an RARα agonist when compared to the situation where the RARα agonist is not used.

Many, if not most, malignancies arise from a rare population of cells that exclusively maintain the ability to self-renew and sustain the tumor. These cancer stem cells are often biologically distinct from the bulk of differentiated cancer cells that characterize the disease. For example, chronic myeloid leukemia (CML) occurs at the level of hematopoietic stem cells and, like their normal counterparts, CML stem cells undergo orderly differentiation. Thus, the bulk of the leukemic mass in CML consists of differentiated blood cells, whereas the rare cells responsible for disease maintenance resemble normal hematopoietic stem cells. Similarly, in multiple myeloma (MM), which is characterized by neoplastic plasma cells, these cells appear to be terminally differentiated like their normal counterparts. The myeloma plasma cells that form the bulk of the tumor arise from a population of less differentiated cancer stem cells that resemble post-germinal center B cells. Other cancers, including but not limited to, hematological malignancies, myelodysplastic syndrome, breast cancer, prostate cancer, pancreatic cancer, colon cancer, ovarian cancer, melanoma, non-melanoma skin cancers, and brain cancers have been demonstrated to arise from corresponding cancer stem cells.

Thus, disclosed herein are methods of treating cancer with agents which can target cancer stem cells in the protected bone marrow niche, or within tumors, by inducing differentiation of the cancer stem cells into mature cancer cells that are susceptible to therapy with CAR-modified immune cells. Previous studies demonstrated that bone marrow stromal cells induce an immature drug-resistant phenotype in multiple myeloma and acute myeloid leukemia cells in the bone marrow. The bone marrow stroma creates a retinoic acid-low (RA-low) environment via CYP26 that prevents the differentiation of normal and malignant cells. Since retinoid signaling promotes PC differentiation and Ig production, modulation of RA signaling is an attractive therapeutic strategy for overcoming drug resistance in the bone marrow microenvironment. Administration of RARα agonists which can act on the cancer stem cells in the bone marrow niche (because they are not inactivated by CYP26), and cause differentiation of the cells (thus rendering them sensitive to killing by CAR-modified immune cells) is one such approach. Such differentiation can also be associated with a change in the cells from being resistant to sensitive to an anti-cancer drug. In some embodiments such an anti-cancer drug is bortezomib. In certain embodiments, effectiveness of therapy with a RARα agonist disclosed herein leads to a substantial decrease in the number of cancer stem cells in the protected environment.

In some embodiments disclosed herein are methods for treating cancer with a combination of one or more RARα agonists and CAR-modified immune cells. Also disclosed herein are methods for treating cancer with a combination of one or more RARα agonists and one or more immune checkpoint targeted cancer therapeutics. Also disclosed herein are methods for treating cancer comprising one or more RARα agonists and one or more immune checkpoint targeted cancer therapeutics and CAR-modified immune cells.

RARα Agonists

Compounds with retinoid activity (vitamin A and its derivatives) have activity in cell proliferation and differentiation processes. Many biological effects of retinoids are mediated by modulating the nuclear retinoic acid receptors (RARs). The RARs activate transcription by binding to DNA sequence elements, known as RAR response elements (RARE), in the form of a heterodimer with one of the retinoid X receptors (known as RXRs). Three subtypes of human RARs have been identified and described: RARα, RARβ, and RARγ.

As used herein, the term "RARα selective agonist" refers to a compound that selectively binds RARα. As used herein, the term "selectively binds," when made in reference to a RARα selective agonist, refers to the discriminatory binding of a RARα selective agonist to the indicated target RARα such that the RARα selective agonist does not substantially bind with non-target receptors like a RARβ or a RARγ. While preferred embodiments make use of a RARα selective agonist, other embodiments can use a RARα agonist that is not necessarily selective for RARα alone. Thus while many embodiments are described as using a RARα selective agonist it should be understood that otherwise similar embodiments using a general RARα agonist are also disclosed.

The term "agonist" as used herein shall be understood to mean a compound which binds to a receptor and activates it, producing gene transcription and a subsequent pharmacological response (e.g., contraction, relaxation, secretion, enzyme activation, etc.). As used herein, the term "RARα agonist" refers to a compound that binds to RARα with a substantially higher affinity compared to binding with another molecule, such as a different RAR. In exemplary embodiments, a RARα agonist is selective for RARα over RARγ and/or RARβ. A RAR selective agonist tends to bind to a particular RAR receptor target with high binding affinity to the near effective exclusion of other RARs. As used herein, the term "agonist" includes selective agonists.

The term "antagonist" as used herein, refers to a compound that attenuates the effect of an agonist by binding in the same site as an agonist without activating the receptor. An antagonist by itself will not affect the gene transcriptional activity of the unoccupied receptor. Conventionally, a RARα antagonist is a chemical agent that inhibits the activity of an RARα agonist. As used herein, the term "antagonist" includes selective antagonists.

The term "inverse agonist" as used herein shall be understood to mean a compound which produces an effect opposite to that of an agonist, yet acts at the same receptor. An inverse agonist by itself will reduce the basal gene transcriptional activity of the unoccupied receptor.

Selective binding of a RARα agonist to a RARα includes binding properties such as, e.g., binding affinity and binding specificity. Binding affinity refers to the length of time a RARα agonist resides at its a RARα binding site, and can be viewed as the strength with which a RARα agonist binds RARα. Binding specificity is the ability of a RARα agonist to discriminate between a RARα and a receptor that does not contain its binding site, such as, e.g., a RARβ or a RARγ. One way to measure binding specificity is to compare the association rate of a RARα agonist for its RARα relative to the association rate of a RARα agonist for a receptor that does not contain its binding site; for example, comparing the association rate constant of a RARα agonist for its RARα relative to a RARβ and/or a RARγ.

In some embodiments, a RARα agonist will have a ratio of activity at a RARα relative to a RARβ and/or a RARγ of, e.g., at least 5 times greater, at least 10 times greater, at least 15 times greater, at least 20 times greater or at least 100 times greater. A RAR pan agonist will have activity at a RARα, a RARβ, and a RARγ, i.e., similar affinity at a RARα, a RARβ, and a RARγ.

The binding specificity of a RARα agonist that selectively binds to a RARα can also be characterized as an activity ratio that such a RARα agonist can exert through binding to its RARα relative to a receptor not comprising its binding site, such as, e.g., a RARβ or a RARγ. In some embodiments, a RARα agonist that selectively binds to a RARα has an activity ratio through its RARα relative to a receptor not comprising its binding site of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1. In some embodiments, a RARα agonist that selectively binds to a RARα has an activity ratio through its RARα relative to a RARβ and/or a RARγ of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

In some embodiments, the RARα agonists useful in the methods disclosed herein are RARα agonists which are not metabolized by CYP26. CYP26 is a cytochrome P450 monooxygenase that metabolizes retinoic acid into inactive, or less active, substances which can also be readily eliminated from cells and regulates cellular levels of retinoic acid. RARα selective agonists that are readily metabolized by CYP26 are not within the scope of these embodiments.

As used herein, the term "CYP26-resistant" refers to RARα agonists (CYP26 metabolism-resistant retinoid means) which are not metabolized, degraded, or otherwise inactivated by the CYP26 enzyme and have activity within the bone marrow.

In an aspect of this embodiment, a RARα agonist is a compound having the structure of formula (I):

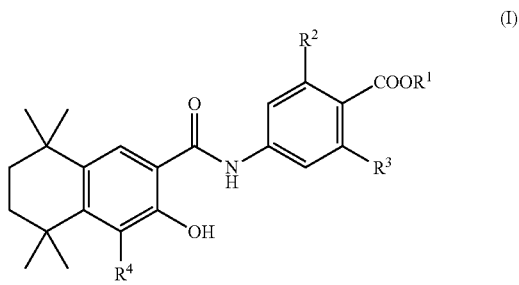

wherein $R^1$ is H or $C_{1-6}$ alkyl, $R^2$ and $R^3$ are independently H or F; and, $R^4$ is a halogen.

In some embodiments of formula I, the halogen is F, Cl, Br or I. In some embodiments, of formula I, the halogen is F. In some embodiments, of formula I, the halogen is Cl. In some embodiments, of formula I, the halogen is Br. In some embodiments, of formula I, the halogen is I.

In an aspect of this embodiment, a RARα agonist is a compound having a structure of formula (II):

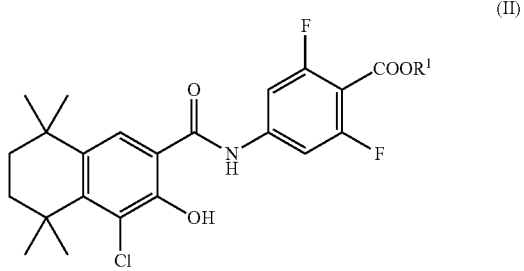

(II)

wherein $R^1$ is H or $C_{1-6}$ alkyl.

In another aspect of this embodiment, a RARα agonist is the compound having the structure of formula (III):

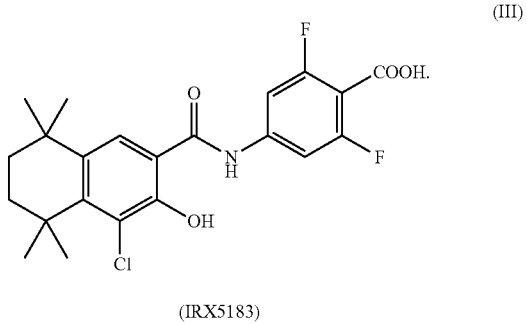

(III)

(IRX5183)

In any embodiment in which $R^1$ is $C_{1-6}$ alkyl, $R^1$ can be $C_1$ alkyl, $C_2$ alkyl, $C_3$ alkyl, $C_4$ alkyl, $C_5$ alkyl, $C_6$ alkyl, or any combination thereof.

In another embodiment, the RARα agonist is tamibarotene (AM80; 4-[(5,6,7,8-tetrahydro-5,5,8,8-tetramethyl-2-naphthalenyl)carbamoyl]benzoic acid). In another embodiment, the RARα agonist is AM580 (4-[(5,6,7,8-tetrahydro-5,5,8,8-tetramethyl-2-naphthalenyl)carboxamido]benzoic acid). In another embodiment, the RARα agonist is Re 80 (4-[1-hydroxy-3-oxo-3-(5,6,7,8-tetrahydro-3-hydroxy-5,5,8,8-tetramethyl-2-naphthalenyl)-1-propenyl]benzoic acid).

Other RARα agonists useful as a compound disclosed herein are described in U.S. Pat. Nos. 5,856,490; 5,965,606; and 6,387,950; each of which is incorporated by reference in its entirety. These references also present data to show that the compounds are indeed RARα agonists. Assays by which a compound can be tested and established to be a RARα agonist are known in the art and are described in numerous prior art publications and patents. For example, a chimeric receptor transactivation assay which tests for agonist-like activity in the RARα, RARβ, RARγ, and RXRα receptor subtypes, is described in detail in U.S. Pat. No. 5,455,265, which is hereby incorporated by reference in its entirety.

Aspects of the present specification provide, in part, a composition comprising a RARα agonist. A RARα agonist includes the compounds disclosed herein.

CAR-Modified Immune Cells

Tumor cells often down-regulate major histocompatibility complex (MHC) expression and furthermore, when they do express MHC alleles, the immunodominant epitopes are not often known. Thus, MHC-dependent cancer immunotherapies are often not effective. Chimeric antigen receptor (CAR)-modified immune cells react with target antigens on cancer cells in an MHC-independent matter. The CAR allows binding via the antigen-binding domain to target cells wherein the CAR-modified cells kill the target cells in a MHC non-restricted manner by binding to the target cells and induction of activation and cytotoxicity of the modified cells against the tumor target. Binding to target cells can also induce proliferation of the CAR-modified cells.

As used herein, the term "target cells" refers to cells expressing a surface antigen that can be bound by the CAR. The antigen can also be referred to as the "target antigen." Target antigens are antigens that are differentially expressed on cancer cells such that the CAR targets the cancer cells preferentially over non-cancer cells.

Once the modified immune cells bind to target antigen, the internal stimulatory domains of the CAR provide the necessary signals for the immune cell to become fully active. In this fully active state, the immune cells can more effectively proliferate and attack cancer cells.

CAR-modified cells can recognize a variety of types of antigen, not only protein but also carbohydrate and glycolipid structures typically expressed on the tumor cell surface. Unlike T cell receptor (TCR) recognition, the antigen does not need to be processed and presented by MHC and therefore the same CAR-molecule can be used in all patients who express the same tumor antigen regardless of HLA type.

The CAR comprises a recombinant polypeptide construct comprising at least an antigen-binding domain, a transmembrane domain, and one or more intracellular stimulatory domains (also referred to as a cytoplasmic signaling domain or an intracellular signaling domain). The antigen-binding domain allows the modified immune cells to specifically bind to the target antigen, the transmembrane domain anchors the CAR in the plasma membrane of the immune cells, and the intracellular stimulatory domain induces persistence, trafficking, and effector functions in the transduced cells.

The antigen-binding domain of a CAR is often derived from a monoclonal antibody, but other ligands (e.g., heregulin, cytokines) and receptors (e.g., NKp30) can also be used. The antigen-binding domain can include an antibody, or a fragment of an antibody that retains antigen-binding function. For example, the CAR antigen-binding domain is often contributed by a single-chain variable fragment (scFv), which is formed from the variable regions of heavy and light chains of an antibody.

In one aspect, the transmembrane domain comprises a sequence of the zeta (ζ) chain associated with the T cell receptor complex, such as the intracellular domain of human CD3 ζ chain.

The one or more intracellular stimulatory domains of the CAR can include an intracellular stimulatory domain of one or more of CD28, 4-1BB (CD137), CD134 (OX-40), ICOS, and CD40L.

The antigen-binding domain, transmembrane domain, and the intracellular stimulatory domain(s) are linked either directly or via a spacer sequence.

The CAR sequences are incorporated in an expression vector. Various expression vectors are known in the art and any such vector may be utilized. In some embodiments, the vector will be a retroviral or lentiviral vector. In other embodiments the vector will be derived from adeno-associated virus.

Immune cells are transformed with the CAR and the CAR is then expressed on the cell surface. Typically, the immune cell stably expresses the CAR, although in some embodiments, the immune cell may transiently express the CAR. The immune cell is thus transfected with a nucleic acid, e.g., mRNA, cDNA, DNA, encoding a CAR. Immune cells of the disclosure include mammalian cells (e.g., human cells), and can be autologous cells, syngeneic cells, allogenic cells, and even in some cases, xenogeneic cells, The cells are engineered to express a CAR and, therefore like the CAR itself, are not found in nature. Exemplary immune cells include T lymphocytes (T cells), natural killer (NK) cells, NKT cells, and macrophages (including monocytes and dendritic cells).

The CAR-modified immune cells are then cultured to expand the population and obtain a suitable number of cells for a single dose or for multiple doses.

In certain embodiments, one or more retinoid and/or rexinoid active agents (e.g. a RARα antagonist, a RARγ agonist, a RXR antagonist, or combinations thereof) are added to the expansion cultures during the culture period and have an effect on the CAR-modified cells directly. For example, in culturing CAR-MIC the one or more retinoid and/or rexinoid active agents added to the expansion cultures would be chosen for their ability to, for example, suppress the development of Treg cells and/or their ability to promote the development Th17 cells. In some embodiments, the one or more retinoid and/or rexinoid active agents are included in the expansion culture of CAR-modified immune cells and administered directly to a subject. This use of retinoid and/or rexinoid active agents is described in U.S. patent application Ser. Nos. 16/034,064 and 16/034,123 which are incorporated by reference herein for all that they teach related to this use.

In certain embodiments, one or more RARα agonists are added to the expansion cultures during the culture period and have an effect on the CAR-modified cells directly. In some embodiments, the one or more RARα agonists are included in the expansion culture of CAR-modified immune cells and administered directly to a subject.

Immune Checkpoint Targeted Cancer Therapeutics

Immune checkpoint therapy targets regulatory pathways in the differentiation and activation of T cells to promote the passage of T cell developmental program through these checkpoints so that anti-tumor (or other therapeutic) activity can be realized. The agents bringing about immune checkpoint therapy are commonly called immune checkpoint inhibitors and it should be understood that it is the check on T cell development that is being inhibited. Thus, while many immune checkpoint inhibitors also inhibit the interaction of receptor-ligand pairs (e.g., anti-PD-1, anti-PD-L1, and CTLA-4), others (such as anti-OX40 and anti-ICOS) act as agonists of targets that release or otherwise inhibit the check on T cell development, ultimately promoting effector function and/or inhibiting regulatory function.

Disclosed herein is the use of immune checkpoint inhibitor molecules in combination with CAR-modified immune cells and RARα agonists. Molecules which inhibit immune checkpoint proteins include antibodies which are specific to one or more of PD-1, PD-1 ligand, CTLA-4, TIM-3, LAG-3, B7-H3, and B7-H4.

Programed death-1 (PD-1) is a checkpoint protein on T cells and normally acts as a type of "off switch" that helps keep the T cells from attacking other cells in the body. It does this by binding to programmed death ligand-1 (PD-L1), a protein on some normal and cancer cells. When PD-1 binds to PD-L1, the T cells will not attack the target cells. Some cancer cells have large amounts of PD-L1, which helps them evade immune attack. Monoclonal antibodies (mAbs) that target either PD-1 or PD-L1 can boost the immune response against cancer cells and have shown a great deal of promise in treating certain cancers. Examples of monoclonal antibodies that target PD-1/PD-L1 include: the anti-PD-1 mAbs nivolumab (OPDIVO®, Bristol-Myers Squibb) and pembrolizumab (KEYTRUDA®, Merck & Co.), BMS-936559 (Bristol-Myers Squibb), pidilizumab (Medivation), and the anti-PD-L1 mAbs durvalumab (MED14736, IMFINZI™, Medimmune), atezolizumab (MPDL3280A; TECENTRIQ®, Hoffman-La Roche), and avelumab (BAVENCIO®, EMD Serono). These antibodies have, variously, demonstrated utility in treating a variety of cancers including malignant melanoma (MM), renal cell carcinoma (RCC), Merkel cell carcinoma, urothelial carcinoma, and non-small cell lung cancer (NSCLC). Non-antibody inhibitors of PD-1/PD-I1 interaction are also being developed; for example, small engineered proteins based on stefin A (called AFFIMER® molecules). In addition to PD-L1, PD-1 can also bind to PD-L2. In addition to PD-1, PD-L1 can also bind to B7-1 (CD80).

CTLA-4 is an immune checkpoint molecule expressed on the surface of CD4 and CD8 T cells and on CD25+FOXP3+ T regulatory (Treg) cells. CTLA-4 generates inhibitory signals that block T cell responses and enables tumor growth. Anti-CTLA-4 mAbs such as ipilimumab (YERVOY®; Bristol-Myers Squibb) cause shrinkage of tumors in animal models. Ipilimumab improves overall survival in MM patients and is approved for the treatment of MM. Responses have been observed in renal cell cancer (RCC) and non small cell lung cacner (NSCLC) as well. Other exemplary anti-CTLA-4 antibodies include tremelimumab (Medimmune).

TIM-3 (T-cell immunoglobulin and mucin-domain containing-3) is a molecule selectively expressed on IFN-γ-producing $CD4^+$ T helper 1 (Th1) and $CD8^+$ T cytotoxic 1 (Tc1) T cells. TIM-3 is an immune checkpoint receptor that functions specifically to limit the duration and magnitude of Th1 and Tc1 T-cell responses. Exemplary antibodies to TIM-3 are disclosed in U.S. Patent Application Publication 20160075783 which is incorporated by reference herein for all it contains regarding anti-TIM-3 antibodies.

LAG-3 (lymphocyte-activation gene 3; CD223) negatively regulates cellular proliferation, activation, and homeostasis of T cells, in a similar fashion to CTLA-4 and PD-1 and plays a role in Treg suppressive function. Exemplary antibodies to LAG-3 include GSK2831781 (GlaxoSmithKline), BMS-986016 (Bristol-Myers Squibb,) and the antibodies disclosed in U.S. Patent Application Publication 2011/0150892 which is incorporated by reference herein for all it contains regarding anti-LAG-3 antibodies.

The B7 family of costimulatory proteins are expressed on the surface of antigen-presenting cells and interact with ligands on T cells. B7-H3 (CD276) is one of the molecules in this family. An antibody to B7-H3, enoblituzumab (EMPLICITI™, Bristol-Myers Squibb) is approved for treatment of multiple myeloma. Another molecule in the family is B7-H4 (V-set domain-containing T-cell activation inhibitor 1), antibodies against which are in development.

Other immune checkpoint inhibitor targets, B- and T-cell attenuator (BTLA), inducible T-cell costimulator (ICOS), OX40 (tumor necrosis factor receptor superfamily, member 4), and others, are potentially useful in the disclosed methods. Several anti-OX40 agonistic mAbs are in early phase cancer clinical trials including MEDI0562 and MEDI6469

(Medimmune), MOXR0916 (Genetech), and PF-04518600 (Pfizer); as is an anti-ICOS agonistic antibody, JTX-2011 (Jounce Therapeutics).

Disclosed herein are methods of treating cancer comprising administering CAR-modified immune cells, one or more RARα agonists, and one or more immune checkpoint targeting immunotherapeutics including a CTLA-4 inhibitor, a PD-1 inhibitor, a TIM-3 inhibitor, a LAG-3 inhibitor, a PD-1 ligand (such as PD-L1), an inhibitor of a PD-1 ligand, an OX40 agonist, an ICOS agonist, a B7-H3 protein, an inhibitor of a B7-H3 protein, a B7-H4 protein, and an inhibitor of a B7-H4 protein. In certain embodiments, the immune checkpoint inhibitors are antibodies.

The immune checkpoint targeting immunotherapeutic antibodies can be whole antibodies or antibody fragments. The terms "fragment of an antibody," "antibody fragment," and "functional fragment of an antibody" are used interchangeably herein to mean one or more fragments of an antibody that retain the ability to specifically bind to an antigen. The antibody fragment desirably comprises, for example, one or more complementary determining regions (CDRs), the variable region (or portions thereof), the constant region (or portions thereof), or combinations thereof. Examples of antibody fragments include, but are not limited to, a Fab fragment, which is a monovalent fragment consisting of the $V_L$, $V_H$, $C_L$, and $CH_1$ domains; a $F(ab')_2$ fragment, which is a bivalent fragment comprising two Fab fragments linked by a disulfide bridge at the hinge region; a Fv fragment consisting of the $V_L$ and $V_H$ domains of a single arm of an antibody; a single chain Fv, in which the $V_L$ and $V_H$ domains are joined by a peptide linker sequence; a Fab' fragment, which results from breaking the disulfide bridge of an $F(ab')_2$ fragment using mild reducing conditions; a disulfide-stabilized Fv fragment (dsFv); and a domain antibody (dAb), which is an antibody single variable region domain (VH or VL) polypeptide that specifically binds antigen. It should also be realized that any of these forms of antigen-binding antibody fragments can provide the antigen binding domain of a CAR.

In alternative embodiments, the immune checkpoint inhibitor antibody is replaced with another protein that similarly binds to the immune checkpoint target molecule. In some instances these non-antibody molecules comprise an extracellular portion of the immune checkpoint target molecule's ligand or binding partner, that is, at least the extracellular portion needed to mediate binding to the immune checkpoint target molecule. In some embodiments this extracellular binding portion of the ligand is joined to additional polypeptide in a fusion protein. In some embodiments the additional polypeptide comprises an Fc or constant region of an antibody.

Methods of Treatment

Provided herein are methods of treating cancer in a mammal by administering one or more RARα agonists and CAR-modified immune cells. In some embodiments, immune checkpoint inhibitors are administered in addition to the CAR-modified immune cells and one or more RARα agonists. Also provided are methods of decreasing tumor burden and/or increasing the disease-free or progression-free survival in subject with cancer. Other embodiments relate to compositions comprising such agents for use in the treatment of cancer and for use in making medicaments for the treatment of cancer. It is to be understood that the multiple agents used may be provided in separate compositions or medicaments which may be administered by separate routes of administration and/or at separate times; nonetheless use of such multiple compositions or medicaments is coordinated so that the patient to whom they are administered receives the benefit of the combined, interacting activity of the multiple agents. For each method of treating cancer disclosed herein there are corresponding methods of cancer immunotherapy. For each method of treating cancer or cancer immunotherapy there are corresponding methods of potentiating cancer treatment/immunotherapy.

In various embodiments one or more RARα agonists are administered to a subject receiving or scheduled to receive CAR-modified immune cells or an immune checkpoint inhibitor. In these embodiments these differentiating RARα agonists (differentiating means) are administered prior to and/or during the interval in which the CAR-modified immune cells or an immune checkpoint inhibitor is present in the subject. It is preferred that the RARα agonist is CYP26-resistant.

In some embodiments, the method comprises administering one or more RARα agonists and CAR-modified immune cells. In some embodiments, the method comprises administering one or more RARα agonists and one or more immune checkpoint inhibitors. In yet other embodiments, the method comprises administering one or more RARα agonist, CAR-modified immune cells, and one or more RARα agonists and one or more immune checkpoint inhibitors. In certain embodiments, the RARα agonist is IRX5183 (AGN195183). With respect to the use of multiple RARα agonists in the various use or method of treatment embodiments described herein, any of the disclosed general formula genera, sub-genera thereof, and individual species may be combined with any other general formula genera, sub-genera thereof, and individual species, each such combination defining an individual embodiment.

The compounds, pharmaceutical compositions, and methods disclosed herein are particularly useful for the treatment of cancer. As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes, but is not limited to, solid tumors and hematologic tumors. The term "cancer" encompasses diseases of skin, tissues, organs, bone, cartilage, blood, and vessels. The term "cancer" further encompasses primary and metastatic cancers. Included within the term "cancer cells" are cancer stem cells.

The disclosed methods can be used to treat any type of cancer known in the art. In certain embodiments, the cancer is a hematologic malignancy. Non-limiting examples of hematologic malignancy include acute myeloid leukemia, chronic myelogenous leukemia (CML), including accelerated CML and CML blast phase, acute lymphoblastic leukemia, chronic lymphocytic leukemia, Hodgkin's disease, non-Hodgkin's lymphoma, including follicular lymphoma and mantle cell lymphoma, B-cell lymphoma, T-cell lymphoma, multiple myeloma, Waldenstrom's macroglobulinemia, myelodysplastic syndromes, including refractory anemia, refractory anemia with ringed sideroblasts, refractory anemia with excess blasts (RAEB), and RAEB in transformation, and myeloproliferative syndromes.

In some embodiments, the cancer is a solid tumor. In other embodiments, the cancer is a solid tumor which can metastasize to the bone. Non-limiting examples of solid tumors that can be treated by the disclosed methods include pancreatic cancer, bladder cancer, colorectal cancer, breast cancer, prostate cancer (e.g., androgen-dependent and androgen-independent prostate cancer), renal cancer, hepatocellular cancer, lung cancer (e.g., non-small cell lung cancer (NSCLC), small cell lung cancer (SCLC), bronchoalveolar carcinoma (BAC), and adenocarcinoma of the lung), ovarian cancer (e.g., progressive epithelial or primary peritoneal cancer), cervical cancer, gastric cancer, esophageal cancer, head and neck cancer (e.g., squamous cell carcinoma of the head and neck), melanoma, neuroendocrine cancer, brain tumors (e.g., glioma, anaplastic oligodendroglioma, adult glioblastoma multiforme, and adult anaplastic astrocytoma), bone cancer, and soft tissue sarcoma.

In select embodiments a particular type of cancer is treated. In other select embodiments a particular type of cancer is excluded from treatment.

Additionally, the one or more RARα agonists can decrease toxicity associated with CAR-modified immune cells by allowing a lower dose of CAR-modified immune cells to be administered with the same efficacy or a higher dose of the CAR-modified immune cells can be administered with the same degree of safety. Intermediate doses between the lower, same efficacy dose and the higher, same safety dose are also envisioned. Thus use of a RARα agonist in coordination with CAR-modified immune cell cancer immunotherapy can lead to the reduction or avoidance of the frequency or severity of toxicities and adverse events related to the activity of the CAR-modified immune cells, or at least the absence of a clinically-relevant increase. By improved or same safety it is meant that the frequency, severity, or both, of one or more toxic or adverse events related to use of CAR-modified immune cells is reduced or at least not increased, respectively. It is to be understood that in the treatment of life-threatening diseases, such as cancer, treatments with potential for substantial toxicity can be considered sufficiently safe.

The cancer stem cells can be enumerated by various mechanisms and reduction in their numbers as a result of administration of a CYP26-resistant RARα agonist measured thereby. In embodiments disclosed herein, as a result of administration of a RARα agonist, the cancer stem cells in the bone marrow are reduced by more than about 0.5 log, more than about 1 log, more than about 1.5 log, more than about 2.0 log, more than about 2.5 log, more than about 3.0 log, more than about 3.5 log, more than about 4.0 log, more than about 4.5 log, or more than about 5.0 log.

The term "treating" or "treatment" broadly includes any kind of treatment activity, including the diagnosis, mitigation, or prevention of disease in man or other animals, or any activity that otherwise affects the structure or any function of the body of man or other animals. Treatment activity includes the administration of the medicaments, dosage forms, and pharmaceutical compositions described herein to a patient, especially according to the various methods of treatment disclosed herein, whether by a healthcare professional, the patient him/herself, or any other person. Treatment activities include the orders, instructions, and advice of healthcare professionals such as physicians, physician's assistants, nurse practitioners, and the like, that are then acted upon by any other person including other healthcare professionals or the patient him/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

A typical dose of CAR-modified immune cells can be, for example, in the range of $1\times10^6$ to $3\times10^{10}$ cells per dose. In some embodiments, CAR-modified immune cells are administered at a dose of at least $1\times10^6$ cells/dose, at least $3\times10^6$ cells/dose, at least $1\times10^7$ cells/dose, at least $3\times10^7$ cells/dose, at least $1\times10^8$ cells/dose, at least $3\times10^8$ cells/dose, at least $1\times10^9$ cells/dose, at least $3\times10^9$ cells/dose, at least $1\times10^{10}$ cells/dose, at least $3\times10^{10}$ cells/dose, or a range defined by any two of the foregoing values. In some embodiments, the typical dose of CAR-modified immune cells can be, for example, in the range of $1\times10^5$ to $1\times10^8$ cells per kilogram of patient body weight. In some embodiments, CAR-modified immune cells are administered at a dose of at least $1\times10^5$ cells/kg, at least $3\times10^5$ cells/kg, at least $6\times10^5$ cells/kg, at least $1\times10^6$ cells/kg, at least $3\times10^6$ cells/kg, at least $6\times10^6$ cells/kg, at least $1\times10^7$ cells/kg, at least $3\times10^7$ cells/kg, or a range defined by any two of the foregoing values.

Therapeutic or prophylactic efficacy can be monitored by periodic assessment of treated patients. For repeated administrations over several days or longer, depending on the condition, the treatment can be repeated until a desired suppression of disease or disease symptoms occurs. However, other dosage regimens may be useful and are within the scope of the present disclosure. The desired dosage can be delivered by a single bolus administration, by multiple bolus administrations, or by continuous infusion administration of the CAR-modified immune cells. In various embodiments the continuous infusion may extend for half an hour, for an hour, for several hours, for a day, or for several days. Treatment may comprise a single or multiple infusions.

In some embodiments, the CAR-modified immune cells are administered with other pre-treatment or simultaneous administrations of additional agents. In some embodiments, subjects who are to receive CAR-modified immune cells are pre-treated with a non-myeloablative, lymphocyte-depleting regiment, such as, but not limited to, treatment with cyclophosphamide and/or fludarabine. In some embodiments, CAR-modified immune cells are administered with interleukin-2.

CAR-modified immune cells may be administered to a subject a single time or multiple times. The cells can be administered weekly, biweekly, monthly, bimonthly, or upon evidence of cancer progression.

"Administering", as used herein, refers to providing a pharmaceutical agent or composition to a subject, and includes, but is not limited to, administering by a medical professional and self-administering. Administration includes, but is not limited to, oral administration, nasal administration, pulmonary administration, subcutaneous administration, intravenous administration, intramuscular administration, intratumoral administration, intracavity administration, intravitreal administration, dermal administration, and transdermal administration, etc.

Depending on the type of cancer, and the patient to be treated, as well as the route of administration, the disclosed RARα selective agonists may be administered at varying therapeutically effective doses to a patient in need thereof.

However, the dose administered to a mammal, particularly a human, in the context of the present methods, should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

As a non-limiting example, when administering a RARα agonist disclosed herein to a mammal, a therapeutically effective amount generally may be in the range of about 1 mg/m$^2$/day to about 100 mg/m$^2$/day. In some embodiments, an effective amount of a RARα agonist disclosed herein may be about 5 mg/m$^2$/day to about 90 mg/m$^2$/day, about 10 mg/m$^2$/day to about 80 mg/m$^2$/day, about 15 mg/m$^2$/day to about 70 mg/m$^2$/day, about 20 mg/m$^2$/day to about 65 mg/m$^2$/day, about 25 mg/m$^2$/day to about 60 mg/m$^2$/day, or about 30 mg/m$^2$/day to about 55 mg/m$^2$/day. In some embodiments, a therapeutically effective amount of a compound or a composition disclosed herein may be at least 10 mg/m$^2$/day, at least 15 mg/m$^2$/day, at least 20 mg/m$^2$/day, at least 25 mg/m$^2$/day, at least 30 mg/m$^2$/day, at least 35 mg/m$^2$/day, at least 40 mg/m$^2$/day, at least 45 mg/m$^2$/day, at least 50 mg/m$^2$/day, at least 55 mg/m$^2$/day, at least 60 mg/m$^2$/day, at least 65 mg/m$^2$/day ,or at least 75 mg/m$^2$/day. In some embodiments, a therapeutically effective amount of a RARα agonist disclosed herein may be at most 15 mg/m$^2$/day, at most 20 mg/m$^2$/day, at most 25 mg/m$^2$/day, at most 30 mg/m$^2$/day, at most 35 mg/m$^2$/day, at most 40 mg/m$^2$/day, at most 45 mg/m$^2$/day, at most 50 mg/m$^2$/day, at most 55 mg/m$^2$/day, at most 60 mg/m$^2$/day, at most 65 mg/m$^2$/day, at most 70 mg/m$^2$/day, at most 80 mg/m$^2$/day, at most 90 mg/m$^2$/day, or at most 100 mg/m$^2$/day.

The average surface area of a human body is generally accepted to be 1.9 m$^2$ for an adult male, 1.6 m$^2$ for an adult female, and 1.33 m$^2$ for a 12-13 year old child. These values can be used to calculate dose ranges for daily dosage for the values in the preceding paragraph. The total daily dosage of RARα agonist can be administered as a single dose or as two doses administered with a 24 hour period spaced 8 to 16, or 10 to 14, hours apart. The RARα agonist(s) are administered in coordination with the CAR-modified immune cells and as above therapeutic or prophylactic efficacy can be monitored by periodic assessment of treated patients. For repeated administrations over several days or longer, depending on the condition, the treatment can be repeated until a desired suppression of disease or disease symptoms occurs. However, other dosage regimens may be useful and are within the scope of the disclosure. The desired dosage can be delivered by a single bolus administration of the composition, by multiple bolus administrations of the composition, or by continuous infusion administration of the composition.

Administration may be continuous or intermittent. The dosage may also be determined by the timing and frequency of administration. Thus, the RARα agonists disclosed herein can be given on a daily, weekly, biweekly, or monthly basis for a period of time, followed by an optional drug holiday (drug free period) and that this drug administration/drug holiday cycle can be repeated as necessary. In certain embodiments, the total daily dosage of RARα agonists can be administered as a single dose or as two doses administered with a 24 hour period spaced 8 to 16, or 10 to 14, hours apart.

The RARα agonists are administered in coordination with the CAR-modified immune cells and as above therapeutic or prophylactic efficacy can be monitored by periodic assessment of treated patients. For repeated administrations over several days or longer, depending on the condition, the treatment can be repeated until a desired suppression of disease or disease symptoms occurs. However, other dosage regimens may be useful and are within the scope of the disclosure. The desired dosage can be delivered by a single bolus administration of the composition, by multiple bolus administrations of the composition, or by continuous infusion administration of the composition.

The RARα agonists can be administered to a mammal using standard administration techniques, including parenteral, oral, intravenous, intraperitoneal, subcutaneous, pulmonary, transdermal, intramuscular, intranasal, buccal, sublingual, or suppository administration. The term "parenteral," as used herein, includes intravenous, intramuscular, subcutaneous, rectal, vaginal, and intraperitoneal administration. The CAR-modified immune cells are administered to a mammal by intravenous, intraperitoneal, or subcutaneous injection. The RARα agonist preferably is suitable for oral administration, for example as a pill, tablet or capsule.

In one embodiment, the RARα agonist is administered daily for a period of time, i.e., at least 1 day, at least 2 days, at least 3 days, at least 4 days, at least 5 days, at least 6 days, at least 1 week, at least 2 weeks, at least 3 weeks, or at least one month, before administration of CAR-modified immune cells. In some embodiments, the RARα agonist is administered starting within 1-7 days of obtaining the patient's peripheral blood lymphocytes for generation of autologous CAR-modified immune cells. CAR-modified immune cells will generally persist in the body for extended periods of time, much longer than will a RARα agonist. It is anticipated that RARα agonist therapy will be administered on a daily basis for a period of time and may be given longer than CAR-modified immune cells. In some embodiments, the RARα is administered for longer than the CAR-modified immune cells, such as for a total of 30 days, 90 days, 1 year, 2 years, 5 years, or more. Alternatively, administration of the RARα agonist may not continue throughout the whole period in which the CAR-modified immune cells persist in the body, and may cease up to a week before, within a day before or after, at the time of, or any of 1-14 days after, administration of the CAR-modified immune cells. The treatment may be conducted in multiple cycles, in which case administration of the RARα agonist can resume prior to the expected administration of CAR-modified immune cells as described above.

Furthermore, CAR-modified immune cells are administered as a single bolus administration, or with daily, weekly, or monthly administrations of 0.5-20×10$^6$ cells per administration.

The CAR-modified immune cells and RARα agonists disclosed herein may be administered in combination with other drugs, such as at least one other anticancer/antineoplastic agent including, for example, any chemotherapeutic agent or targeted therapy agent known in the art, ionizing radiation, small molecule anticancer agents, cancer vaccines, biological therapies (e.g., other monoclonal antibodies, cancer-killing viruses, gene therapy, and adoptive T-cell transfer), and/or surgery. In other embodiments the CAR-modified immune cells and RARα agonists are the only therapeutic reagents administered or the only treatment given; or the only treatment or reagents given, the primary utility of which is to promote an anti-cancer immune response.

In some exemplary embodiments treatment is initiated with administration of a RARα agonist. In some embodiments the RARα agonist is CYP26-resistant. Concurrent with or subsequent to administration of the RARα agonist, CAR-MIC, and optionally an antineoplastic agent, is administered, concurrently or sequentially. In some aspects of these embodiments the antineoplastic agent, if used, is administered prior to administration of the CAR-MIC. The antineoplastic agent is administered for an interval of 1 day to 1 month, for example, 2 days, 5 days, 1, 2, 3, or 4 weeks. In some embodiments, administration of the antineoplastic agent ceases 1 day to 1 week prior to administration of the CAR-MIC. In some embodiments the CAR-MIC is a CAR-T cell. In some embodiments the antineoplastic agent is bortezomib. In various aspects of these embodiments the cancer can be a myeloma, such as multiple myeloma, or a leukemia, such as AML, CML, or acute promyelocytic leukemia (APL). In a further aspect of these embodiments the RARα agonist can be formula (III) (IRX5183).

The effectiveness of cancer therapy is typically measured in terms of "response." The techniques to monitor responses can be similar to the tests used to diagnose cancer such as, but not limited to:

A lump or tumor involving some lymph nodes can be felt and measured externally by physical examination.

Some internal cancer tumors will show up on an x-ray or CT scan and can be measured with a ruler.

Blood tests, including those that measure organ function can be performed.

A tumor marker test can be done for certain cancers.

Regardless of the test used, whether blood test, cell count, or tumor marker test, it is repeated at specific intervals so that the results can be compared to earlier tests of the same type.

Response to cancer treatment is defined several ways:

Complete response—all of the cancer or tumor disappears; there is no evidence of disease. Expression level of tumor marker (if applicable) may fall within the normal range.

Partial response—the cancer has shrunk by a percentage but disease remains. Levels of a tumor marker (if applicable) may have fallen (or increased, based on the tumor marker, as an indication of decreased tumor burden) but evidence of disease remains.

Stable disease—the cancer has neither grown nor shrunk; the amount of disease has not changed. A tumor marker (if applicable) has not changed significantly.

Disease progression—the cancer has grown; there is more disease now than before treatment. A tumor marker test (if applicable) shows that a tumor marker has risen.

Other measures of the efficacy of cancer treatment include intervals of overall survival (that is time to death from any cause, measured from diagnosis or from initiation of the treatment being evaluated)), cancer-free survival (that is, the length of time after a complete response cancer remains undetectable), and progression-free survival (that is, the length of time after disease stabilization or partial response that resumed tumor growth is not detectable).

There are two standard methods for the evaluation of solid cancer treatment response with regard to tumor size (tumor burden), the WHO and RECIST standards. These methods measure a solid tumor to compare a current tumor with past measurements or to compare changes with future measurements and to make changes in a treatment regimen. In the WHO method, the solid tumor's long and short axes are measured with the product of these two measurements is then calculated; if there are multiple solid tumors, the sum of all the products is calculated. In the RECIST method, only the long axis is measured. If there are multiple solid tumors, the sum of all the long axes measurements is calculated. However, with lymph nodes, the short axis is measured instead of the long axis.

In some embodiments of the current method, the tumor burden of a treated patient is reduced by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 1-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 5-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 10-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In yet other embodiments, the subject has a sustained remission of at least 6 months, at least 7 months, at least 8 months, at least 9 months, at least 10 months, at least 11 months, at least 12 months, at least 14 months, at least 16 months, at least 18 months, at least 20 months, at least 22 months, at least 24 months, at least 27 months, at least 30 months, at least 33 months, at least 36 months, at least 42 months, at least 48 months, at least 54 months, or at least 60 months or more.

In other embodiments, the method may help to treat or alleviate conditions, symptoms, or disorders related to cancer. In some embodiments, these conditions or symptoms may include, but are not limited to, anemia, asthenia, cachexia, Cushing's Syndrome, fatigue, gout, gum disease, hematuria, hypercalcemia, hypothyroidism, internal bleeding, hair loss, mesothelioma, nausea, night sweats, neutropenia, paraneoplastic syndromes, pleuritis, polymyalgia rheumatica, rhabdomyolysis, stress, swollen lymph nodes, thrombocytopenia, Vitamin D deficiency, or weight loss. In other embodiments, the administration of both the RARα agonist and CAR-modified immune cells prolongs the survival of the individual being treated relative to treatment with the CAR-modified immune cells alone.

List of Particular Embodiments

The following listing of embodiments is illustrative of the variety of embodiments with respect to breadth, combinations and sub-combinations, class of invention, etc., elucidated herein, but is not intended to be an exhaustive enumeration of all embodiments finding support herein.

Embodiment 1. A method of cancer immunotherapy comprising administering to a subject in need thereof chimeric antigen receptor-modified immune cells (CAR-MIC) and at least one differentiating RAR active agent.

Embodiment 2. A method of treating cancer comprising administering to a subject in need thereof (CAR-MIC) and at least one differentiating RAR active agent.

Embodiment 3. A method of potentiating CAR-MIC cancer immunotherapy comprising administering at least one differentiating RAR active agent to a cancer patient who is receiving, has received, or is scheduled to receive CAR-MIC.

Embodiment 4. A method of cancer immunotherapy comprising administering to a subject in need thereof, a differentiating RAR active agent and CAR-MIC, wherein the CAR-MIC are cultured in a culture medium comprising at least one immunomodulatory RAR/RXR active agent prior to being administered to the subject.

Embodiment 5. A method of prolonging the disease-free survival of a cancer patient comprising administering CAR-MIC and at least one differentiating RAR active agent.

Embodiment 6. A method of decreasing toxicity of CAR-MIC therapy comprising administering to a subject in need thereof at least one differentiating RAR active agent in combination with the CAR-MIC such that as a result of the combination, a lower dose of CAR-MIC are administered than if the CAR-MIC were administered alone.

Embodiment 7. The method of Embodiment 6, wherein the efficacy is the same or increased as compared to the administration of CAR-MIC alone.

Embodiment 8. A method of increasing efficacy of CAR-MIC therapy comprising administering to a subject in need thereof at least one differentiating RAR active agent in combination with the CAR-MIC such that as a result of the combination, a higher dose of CAR-MIC are administered than if the CAR-MIC were administered alone.

Embodiment 9. The method of Embodiment 8, wherein the toxicity is the same or decreased as compared to the administration of CAR-MIC alone.

Embodiment 10. The method of any one of Embodiments 1-9, further comprising administration of an immune checkpoint inhibitor.

Embodiment 11. The method of Embodiment 10 wherein the immune checkpoint inhibitor is an inhibitor of at least one of CTLA-4, PD-1, TIM-3, LAG-3, PD-L1 ligand, B7-H3, B7-H4, BTLA, or is an ICOS, or OX40 agonist.

Embodiment 12. The method of Embodiment 10 or 11, wherein the immune checkpoint inhibitor is an antibody.

Embodiment 13. The method of any one of Embodiments 1-12, wherein the differentiating RAR active agent is a RARα agonist.

Embodiment 14. The method of Embodiment 12, wherein the RARα agonist is CYP26-resistant.

Embodiment 15. The method of Embodiment 12 or 13, wherein the RARα agonist is a RARα selective agonist.

Embodiment 16. The method of any one of Embodiments 13-15, wherein the RARα agonist is a compound of general formula (V):

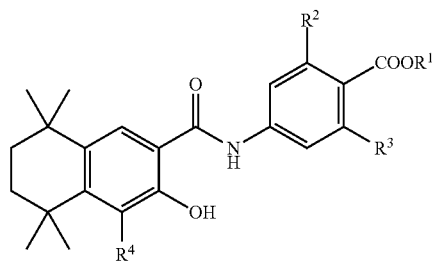

wherein $R^1$ is H or $C_{1-6}$ alky, $R^2$ and $R^3$ are independently H or F, and $R^4$ is a halogen.

Embodiment 17. The method of Embodiment 16, wherein $R^4$ is F, CL, BR, or I.

Embodiment 18. The method of any one of Embodiments 13-15, wherein the RARα agonist is a compound of general formula (VI):

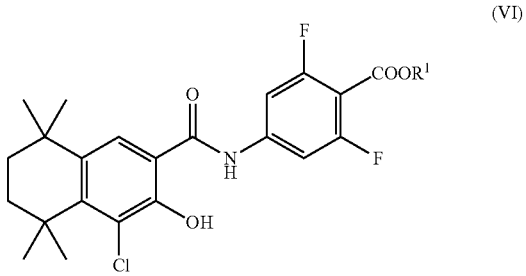

wherein $R^1$ is H or $C_{1-6}$ alkyl.

Embodiment 19. The method of any one of Embodiments 13-15, wherein the RARα agonist is a compound of general formula (III):

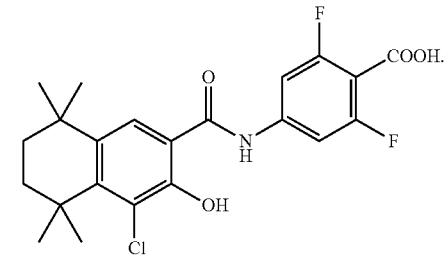

(III; IRX5183)

Embodiment 20. The method of any one of Embodiments 13-14, wherein the RARα agonist is tamibarotene (AM80; 4-[(5,6,7,8-tetrahydro-5,5,8,8-tetramethyl-2-naphthalenyl) carbamoyl]benzoic acid).

Embodiment 21. The method of any one of Embodiments 13-14, wherein the RARα agonist is AM580 (4-[(5,6,7,8-tetrahydro-5,5,8,8-tetramethyl-2-naphthalenyl)carboxamido]benzoic acid).

Embodiment 22. The method of any one of Embodiments 13-14, wherein the RARα agonist is Re 80 (4-[1-hydroxy-3-oxo-3-(5,6,7,8-tetrahydro-3-hydroxy-5,5,8,8-tetramethyl-2-naphthalenyl)-1-propenyl]benzoic acid).

Embodiment 23. The method of any one of Embodiments 1-22, wherein the differentiating RAR active agent or RARα agonist is administered daily.

Embodiment 24. The method of any one of Embodiments 1-22, wherein the differentiating RAR active agent or RARα agonist is administered twice a day.

Embodiment 25. The method of Embodiment 23 or 24, wherein the daily dosage of RAR active agent or RARα agonist is in a range of from about 1, 5, 10, 15, 20, 25, 30, 35, 40, 45, 50, 55, 60, 65, 70, or 75 mg/m$^2$/day, to about 15, 20, 25, 30 ,35, 40, 45, 50, 55, 60, 65, 70, 75, 80, 85, 90, 95, or 100 mg/m$^2$/day, the endpoints of the range selected so that the low end of the range is less than or equal to the high end of the range.

Embodiment 26. The method of any one of Embodiments 1-25, further comprising administering at least one cancer chemotherapy or targeted therapy agent.

Embodiment 27. The method of Embodiment 26, wherein the at least one cancer chemotherapy or targeted therapy agent is bortezomib.

Embodiment 28. The method of any one of Embodiments 1-26, wherein the subject or cancer patient has a hematologic malignancy.

Embodiment 29. The method of Embodiment 28, wherein the hematologic malignancy is selected from acute myeloid leukemia, chronic myelogenous leukemia (CML), including accelerated CML and CML blast phase, acute lymphoblastic leukemia, chronic lymphocytic leukemia, Hodgkin's disease, non-Hodgkin's lymphoma, including follicular lymphoma and mantle cell lymphoma, B-cell lymphoma, T-cell lymphoma, multiple myeloma, Waldenstrom's macroglobulinemia, myelodysplastic syndromes, including refractory anemia, refractory anemia with ringed sideroblasts, refractory anemia with excess blasts (RAEB), and RAEB in transformation, and myeloproliferative syndromes.

Embodiment 30. The method of Embodiment 28 or 29, wherein the hematologic malignancy is a leukemia.

Embodiment 32. The method of Embodiment 28 or 29, wherein the hematologic malignancy is multiple myeloma.

Embodiment 33. The method of any one of Embodiments 1-26, wherein the subject or cancer patient has a solid tumor.

Embodiment 34 The method of Embodiment 33, wherein the pancreatic cancer, bladder cancer, colorectal cancer, breast cancer, prostate cancer (e.g., androgen-dependent and androgen-independent prostate cancer), renal cancer, hepatocellular cancer, lung cancer (e.g., non-small cell lung cancer (NSCLC), small cell lung cancer (SCLC), bronchoalveolar carcinoma (BAC), and adenocarcinoma of the lung), ovarian cancer (e.g., progressive epithelial or primary peritoneal cancer), cervical cancer, gastric cancer, esophageal cancer, head and neck cancer (e.g., squamous cell carcinoma of the head and neck), melanoma, neuroendocrine cancer, brain tumors (e.g., glioma, anaplastic oligodendroglioma, adult glioblastoma multiforme, and adult anaplastic astrocytoma), bone cancer, and soft tissue sarcoma.

Embodiment 35. The method of any one of Embodiments 1-34, wherein the differentiating RAR active agent or RARα agonist is administered for at least 1 day, at least 2 days, at least 3 days, at least 4 days, at least 5 days, at least 6 days, at least 1 week, at least 2 weeks, at least 3 weeks, or at least one month, before administration of CAR-MIC.

Embodiment 36 The method of Embodiment 35, wherein administration of the differentiating RAR active agent or RARα agonist is discontinued prior to administration of CAR-MIC, for example, 2 to 10 days prior to administration of CAR-MIC.

Embodiment 37. The method of Embodiment 35, wherein administration of the differentiating RAR active agent or RARα agonist is discontinued prior to administration of CAR-MIC, for example, at a point in an interval from 2 days prior to 2 days subsequent to administration of CAR-MIC.

Embodiment 38. The method of Embodiment 35, wherein administration of the differentiating RAR active agent or RARα agonist is continued for an interval subsequent to administration of CAR-MIC greater than 2 days.

Embodiment 39. The method of Embodiment 38, wherein administration of the differentiating RAR active agent or RARα agonist is discontinued 14 days subsequent to administration of CAR-MIC.

Embodiment 40. The method of any one of Embodiments 35-39, wherein the differentiating RAR active agent or RARα agonist is administered for a period of time beginning 4 weeks before administration of CAR-MIC is scheduled to begin.

Embodiment 41. A method of treatment constituting multiple cycles of treatment, wherein any one of Embodiments 35-40 constitutes one cycle.

Embodiment 42. The method of any one of Embodiments 35-41, in which administration of the differentiating RAR active agent or RARα agonist having been discontinued, wherein administration of the differentiating RAR active agent or RARα agonist is resumed prior to a scheduled further administration of CAR-MIC.

Embodiment 43. The method of Embodiment 42 wherein the differentiating RAR active agent or RARα agonist is administered for at least 2 days, at least 3 days, at least 4 days, at least 5 days, at least 6 days, at least 1 week, at least 2 weeks, at least 3 weeks, or at least one month, before administration of the CAR-MIC.

Embodiment 44. The method of any one of Embodiments 41-43, wherein cycles of treatment continue for at least 6 months following 1st administration of the CAR-MIC.

Embodiment 45. The method of any one of Embodiments 41-43, wherein cycles of treatment continue until a durable complete response is obtained.

Embodiment 46. The method of any one of Embodiments 41-43, wherein cycles of treatment continue as long as there is continued tumor regression.

Embodiment 47. The method of any one of Embodiments 41-43, wherein cycles of treatment continue as long as there is stable disease or the cancer does not progress.

Embodiment 48. The method of Embodiment 45 or 47, wherein treatment is suspended following the attainment of complete response or stable disease and cycles of treatment resume upon disease progression.

Embodiment 49. The method of any one of Embodiments 1-48, wherein the CAR-MIC are administered by intravenous injection or infusion.

Embodiment 50. The method of any one of Embodiments 1-48, wherein the CAR-MIC are administered by intratumoral injection.

Embodiment 51. The method of any one of Embodiments 1-50, wherein $1\times10^6$ to $3\times10^{10}$ cells are administered.

Embodiment 52. The method of Embodiment 1-51, wherein $1\times10^5$ to $1\times10^8$ cells per kilogram of patient body weight are administered.

Embodiment 53. The method of any one of Embodiments 1-52, wherein the CAR-MIC is a CAR-T cell.

Embodiment 54. The method of any one of Embodiments 1-52, wherein the CAR-MIC is a CAR-NKT cell.

Embodiment 55. The method of any one of Embodiments 1-52, wherein the CAR-MIC is a CAR-macrophage.

Embodiment 56. A differentiating RAR active agent for use in reducing the toxicity of CAR-MIC therapy.

Embodiment 57. A differentiating RAR active agent for use in potentiating the immunotherapeutic effect of CAR-MIC in the treatment of cancer.

Embodiment 58. CAR-MIC and a differentiating RAR active agent for use in treating cancer.

Embodiment 59. CAR-MIC and a differentiating RAR active agent for use in cancer immunotherapy.

Embodiment 60. The differentiating RAR active agent for use according to Embodiment 56 or 57, or the CAR-MIC and a differentiating RAR active agent for use according to Embodiment 58 or 59, in a cancer patient who is receiving, has received, or is scheduled to receive, CAR-MIC.

Embodiment 61. Use of a differentiating RAR active agent in the manufacture of a medicament for potentiating the immunotherapeutic effect of CAR-MIC in the treatment of cancer.

Embodiment 62. Use of CAR-MIC and a differentiating RAR active agent in the manufacture of medicaments for cancer immunotherapy.

Embodiment 63. Use of CAR-MIC and a differentiating RAR active agent in the manufacture of medicaments for prolonging the disease-free survival of a cancer patient.

Embodiment 64. Use of a differentiating RAR active agent in the manufacture of a medicament for reducing the toxicity of CAR-MIC therapy.

Embodiment 65. Use of CAR-MIC and a differentiating RAR active agent in the manufacture of medicaments for treating cancer.

Embodiment 66. The use of any one of embodiments 61-65, wherein the differentiating RAR active agent medicament is for use in a cancer patient who is receiving, has received, or is scheduled to receive, CAR-MIC.

It should be manifest that each of Embodiments 56-66 can be modified in a manner similar to the modification of Embodiments 1-6 by embodiments 7-55.

EXAMPLES

The following non-limiting examples are provided for illustrative purposes only in order to facilitate a more complete understanding of representative embodiments now contemplated. These examples should not be construed to limit any of the embodiments described in the present specification.

Example 1

Binding of Test Compounds to RAR Receptors and Activation of Reporter Genes

Retinoic acid receptor transactivation activity and binding efficiencies are determined essentially as described in U.S. Pat. Nos. 5,298,429 and 5,071,773, incorporated by reference herein. Transactivation assays employ expression plasmids encoding the full length receptors RARα, RARβ, and RARγ. Reporter plasmids containing the herpes virus thymidine kinase promoter and the appropriate retinoic acid receptor response element (RAREs) are positioned upstream of an open coding region encoding firefly luciferase.

Binding assays are performed using a classic competition assay format in which cloned receptor RAR molecules are first loaded with radiolabeled all-trans-retinoic acid (RAR) and then the amount of radioactivity liberated with increasing concentration of test compound is measured.

The assays are used to identify RARα agonists as disclosed herein above.

Example 2

Compound IRX5183 is RARα Specific

To determine whether the compounds having a structure of formula I are RARα selective agonists, the compound IRX5183 was examined for its ability to bind to RARα, RARβ, and RARγ using a displacement assay to measure agonist binding affinity and a transactivation assay to measure agonist activity (described in U.S. Pat. No. 5,455,265, which is hereby incorporated by reference). These results indicate that compound IRX5183 selectively binds to RARα with high affinity (Table 1) and specifically activates RARα (FIG. 1. Such a RARα selective agonist could minimize the adverse effects related to pan-activation including mucocutaneous toxicity, headache, and proinflammatory events in clinical studies.

TABLE 1

IRX5183 Binding Affinities for RARα, RARβ, and RARγ

| RARα | RARβ | RARγ |
| --- | --- | --- |
| 4.7 nM | >10,000 nM | >10,000 nM |

Example 3

RARα Signaling induces Foxp3 Expression

Figure 2A:
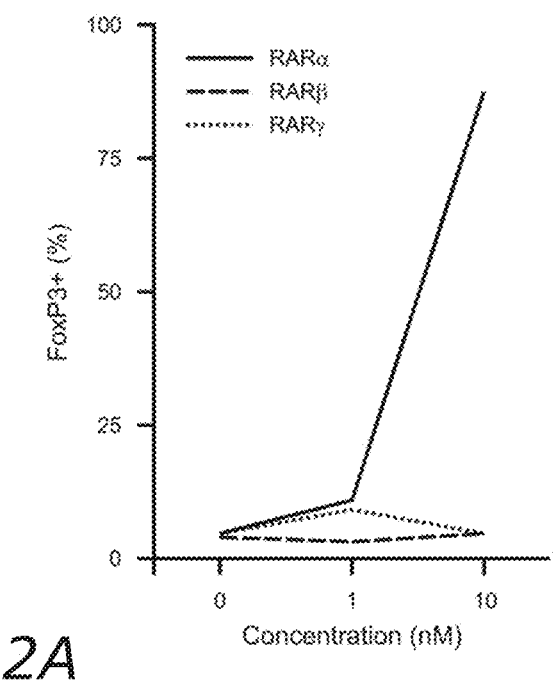
FIG. 2A-C shows that RAR receptor specific agonists regulate FoxP3, α4β7, and CCR9 expression. Purified CD4$^+$ CD25- FoxP3-cells were cultured in media with the specified concentration of each RAR agonist and analyzed by flow cytometry for FoxP3 (FIG. 2A), α4β7 (FIG. 2B), and CCR9 (FIG. 2C) expression in total CD4 T cells. FoxP3 results are representative of three independent experiments. CCR9 and α4β7 results are representative of multiple experiments.
Figure 2B:
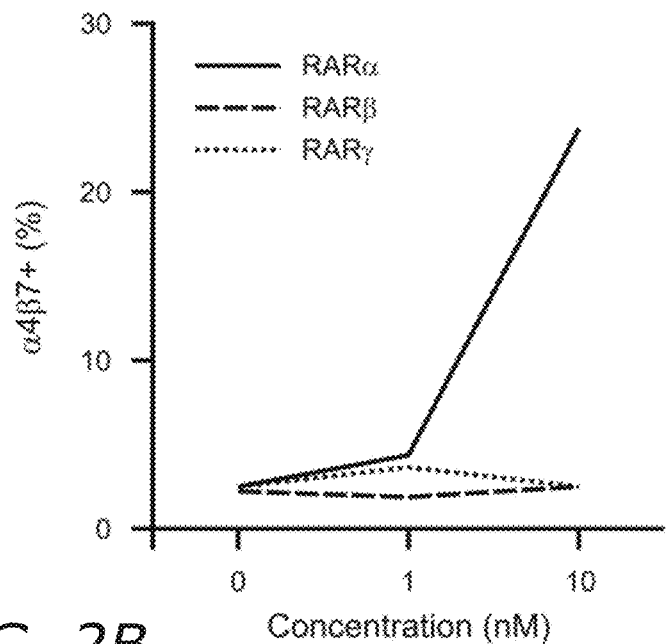
Figure 2C:
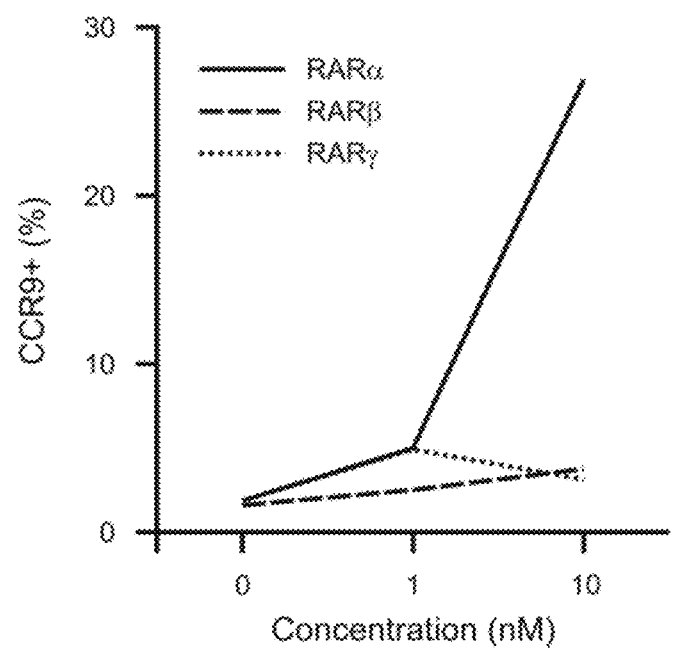

To determine which of the RAR (RARα, RARβ, RARγ) signaling pathways is involved in the induction of Foxp3 expression, naive CD4$^+$ CD25$^-$ FoxP3$^-$ cells were purified from a Foxp3-GFP mouse using flow cytometry by sorting and isolating based upon a GFP$^-$ phenotype. These cells were activated polyclonally with αCD3 in vitro in the presence of IL-2 and TGF-β. To identify the RAR involved in RA-induced Foxp3 expression, the cultured cells were incubated with RAR selective agonists. The cultured cells were then scored for the frequency of GFP$^+$ (Foxp3$^+$). With respect to the use of selective agonists, only the RARα agonist exerted significant impact on the expression of Foxp3 inducing nearly 100% Foxp3+ T cells, with enhancement on the expression of α4β7 and CCR9 (gut homing receptors) (FIG. 2). The RARγ and RARβ agonists were without effect.

Example 4

RARα Selective Agonists Regulates T Cell Differentiation

To determine whether a RARα agonist could affect T cell differentiation, T cells were incubated with a RARα agonist to determine its effect on Foxp3 expression. Naive CD4$^+$ CD25$^-$ FoxP3$^-$ cells were purified from a Foxp3-GFP mouse using flow cytometry by sorting and isolating based upon a GFP$^-$ phenotype. These cells were activated polyclonally with αCD3 in vitro in the presence of IL-2 and TGF-β. These cells were then cultured in media with various concentrations of compound IRX5183 (a RARα agonist) and the expression of FoxP3-GFP was analyzed by flow cytometry. The RARα agonist compound IRX5183 enhanced differentiation of immunosuppressive Treg cells and inhibited differentiation of inflammatory TH17 cells from naïve T cells in vitro (Table 2).

TABLE 2

RARα agonist Effects on T Cell Differentiation

| RARα agonist | Treg cell | | Th17 cell | |
|---|---|---|---|---|
| | Concentration (nM) | Percent Differentiation (%) | Concentration (nM) | Percent Differentiation (%) |
| Compound IRX5183 | 0 | 25 | 0 | 32 |
| | 0.1 | 26 | 0.1 | 32 |
| | 1 | 55 | 1 | 21 |
| | 10 | 90 | 10 | 11 |
| | 100 | ND | 100 | 5 |

To expand on the finding above, the in vivo effects of a RARα agonist on T cell differentiation was evaluated in a mouse model. Mice were treated with 100 μg of compound IRX5183 or an equivalent volume of DMSO (vehicle control) every other day for 10 days. Lymphocytes from the blood and spleen were then isolated and FoxP3 expression in CD4+ T cells was assessed. The data shows that following administration of compound IRX5183 there was a significant increase in the percentage of Foxp3+ T cells in the spleen and blood of treated mice (Table 3).

TABLE 3

RARα Agonist Effects on T Cell Differentiation

| Tissue | Foxp3+ Expression (%) | |
|---|---|---|
| | DMSO | IRX5183 |
| Blood | 2.4 | 4.3 |
| Spleen | 10 | 25 |

Conversely, AGN196996, an RARα selective antagonist, increases Th17 cell numbers and decreases Treg cell numbers in the above in vitro and in vivo assays (data not shown).

Example 5

The Bone Marrow Niche Induces a Bortezomib Resistance in Multiple Myeloma

Multiple myeloma (MM) is characterized by the proliferation of malignant plasma cells (PCs) within the BM and their production of monoclonal immunoglobulin (Ig). Novel therapies, including proteasome inhibitors, have significantly extended the survival of patients with MM but have failed to achieve a cure. Increasing evidence demonstrates that interactions with the BM microenvironment play a critical role in the survival of MM cells during chemotherapy. However, the mechanisms mediating this BM niche-dependent chemoprotection are incompletely understood and remain a critical area of research.

Certain MM cells that resemble mature B cells and are resistant to bortezomib (BTZ). Like their normal B cell counterparts, these CD138− MM cells are capable of clonogenic growth and differentiation into CD138+ PCs. Moreover, these cells are enriched during minimal residual disease (MRD), suggesting a critical role in disease relapse. Differential BTZ sensitivity of CD138+ and CD138− MM cells may be explained by their secretory activity. As a result of their abundant Ig production, CD138+ PCs are highly dependent on an intact proteasome pathway to degrade improperly folded proteins. Conditions that disrupt protein degradation by the proteasome activate a cellular stress pathway known as the unfolded protein response (UPR), which counteracts ER stress by decreasing protein synthesis and promoting protein degradation. If homeostasis cannot be reestablished, UPR activation eventually leads to apoptosis. On the other hand, CD138− MM cells exhibit limited Ig production and low ER stress and are less dependent on proteasome-mediated degradation of misfolded proteins.

Previous studies demonstrated that BM stromal cells induce an immature drug-resistant phenotype in MM. BM stroma creates a retinoic acid-low (RA-low) environment via CYP26 that prevents the differentiation of normal and malignant cells. Since retinoid signaling promotes PC differentiation and Ig production, this study determined whether the BM niche via stromal CYP26 activity induces BTZ resistance by preventing PC differentiation (Alonso S. et al., J. Clin. Invest. 126:4460-4468, 2016). An RA-low environment induced by stromal CYP26 is responsible for maintaining a B cell-like, BTZ-resistant phenotype in MM cells. Directly inhibiting CYP26 or bypassing stromal protection via a CYP26-resistant retinoid rescues PC differentiation and BTZ sensitivity. Furthermore, we describe a bidirectional crosstalk, in which paracrine Hedgehog secreted by MM cells reinforces a protective niche via an increase in the ability of BM stroma to inactivate RA. These data indicate that modulation of RA signaling is an attractive therapeutic strategy for overcoming BTZ resistance in the MM BM microenvironment.

Methods

Cell cultures. All cell lines were purchased from the American Type Culture Collection. H929, MM.1S, and U266 cells were cultured in RPMI 1640 with 10% FCS (Fetal Calf Serum), 2 mM L-glutamine, and 100 μg/ml penicillin-streptomycin (P/S). OP-9 cells were cultured in α-MEM, 20% FCS, L-glutamine, and P/S. Cell lines were authenticated by short-tandem repeat profiling.

Primary MM cells were obtained from patients with newly diagnosed or relapsed MM under an IRB-approved protocol. Briefly, mononuclear cells were isolated from fresh BM aspirates by density gradient centrifugation (Ficoll-Paque); CD138+ cells were then selected via magnetic beads and columns and incubated in RPMI 1640, 10% FCS, L-glutamine, and P/S at 37° C.

Primary human BM stromal cells were derived from aspirates collected from healthy donors under an IRB-approved protocol. Briefly, total mononuclear cells isolated from BM aspirates were cultured in Iscove's modified Dulbecco's medium (IMDM) supplemented with 10% horse serum, 10% FCS, $10^{-5}$ M hydrocortisone 21-hemisuccinate, P/S, and 0.1 mM β-mercaptoethanol (β-ME) (FBMD1 media). The following day, cells in suspension were removed by washing twice with PBS, and the media were replaced. Attached stromal cells were incubated at 33° C. until a confluent monolayer was obtained. Mouse primary BM stromal cells were isolated following the same protocol, after isolation of total BM mononuclear cells from mouse femurs.

Vectors and viral supernatants. To generate Smo-KO and WT stroma, BM stromal cells were derived from Smo$^{fl/fl}$ mice and transduced with the retroviral vector PIG-Cre encoding Cre-recombinase (Addgene; catalog 50935) or a control vector (Addgene; catalog 18751), respectively. Successfully infected cells were selected using 4 μg/ml puromycin for 5 days and confirmed by expression of GFP via flow cytometry. The pLenti-CMV-LUC-Puro lentiviral vector (plasmid 17477) was used to generate H929 Luc+ cells.

To generate CYP26A1-overexpressing stromal cells, WT and Smo-KO stromal cells were transduced with the lentiviral vector pBABE-neo (Addgene; catalog 1767) that had been engineered to encode CYP26A1. Briefly, Cyp26a1 cDNA (Origene) was amplified via PCR using primers incorporating the restriction sites BamHI and EcoRI and cloned into the pCR2.1 vector. Cyp26a1 cDNA was confirmed via Sanger sequencing, and the fragment was isolated after digestion with the restriction enzymes BamHI and EcoRI and subcloned into the corresponding sites of the pBABE vector. Lentiviral particles were produced as previously described. Successfully infected stromal cells were selected using 3 μg/ml G-418 for 10 days, and expression of Cyp26a1 was confirmed by qRT-PCR.

Coculture experiments. 24-well plates were coated with 0.1% gelatin in PBS for 30 min at 37° C. The gelatin solution was removed, and the stromal cells were cultured overnight at a density of $5 \times 10^4$ cells/well to obtain a confluent monolayer. At that time, MM cell lines or primary MM cells ($1 \times 10^5$ in 2 ml) were added to the stroma cultures. The stroma cocultures were incubated at 37° C. in RPMI containing 10% FCS, L-glutamine, and P/S, with or without AGN194310 (1 μM for 5 days), R115866 (1 μM for 5 days), IRX5183 (1 μM for 5 days), or BTZ (2.5 nM for 48 hr).

Transwell experiments. For Transwell experiments, 6-well plates were coated with 0.1% gelatin in PBS for 30 min at 37° C. The gelatin solution was removed, and the stromal cells were cultured overnight in FBMD1 media at a density of $10 \times 10^4$ cells/well in 2 ml of media to obtain a confluent monolayer. At that time, Transwell inserts (Corning) were placed over the stroma cultures, and MM cell lines ($1 \times 10^6$ in 1 ml) were seeded in the Transwell for 24 hr at 37° C. Following this incubation, Transwell and MM cells were removed, and stromal cells were detached from the wells and analyzed by qRT-PCR for CYP26 expression.

Mobilization experiments. MM cells were separated from BM stromal cells by gently pipetting several times around the well. Detached cells were centrifuged, resuspended in fresh media, and incubated in a 24-well plate for 1 hr at 37° C. During this short incubation period, contaminating stromal cells attached to the well, while MM cells remained in suspension. MM cells were then recovered by gently pipetting. This protocol was used for qRT-PCR and CFU coculture experiments. The purity achieved using this protocol was confirmed by flow cytometry to be 98%-99% MM cells and less than 2% contaminating stroma.

Clonogenic assays. After treatment, MM cells were collected, washed with PBS, and plated at a density of 5,000 cells/ml in 1 ml of 1.32% methylcellulose supplemented with 30% FBS, 10% BSA, L-glutamine, P/S, and 0.1 mM β-ME. Cells were plated in triplicate in 35-mm culture dishes, incubated at 37° C., and scored for the presence of colonies 14 days later.

qRT-PCR. Total RNA was extracted using the RNeasy Mini Kit (QIAGEN) according to the manufacturer's instructions. cDNA was synthesized by reverse transcription using the iScript cDNA Synthesis Kit (Bio-Rad). qRT-PCR was performed with iTaq SYBR Green Supermix (Bio-Rad) using sequence specific primers. Gene expression was normalized to GAPDH, and relative quantification was calculated using $\Delta\Delta Ct$. All experiments were performed in duplicate and run on the Bio-Rad CFX96 machine.

Flow cytometry. Following treatment, MM cells were collected, washed with PBS, and stained for 15 min at room temperature with phycoerythrin-conjugated (PE-conjugated) anti-CD138. Cells were washed to remove unbound antibody and evaluated in a FACSCalibur system (BD Biosciences). Stromal cells were identified by GFP expression, and viable cells were identified using 7-aminoactinomycin D (7-AAD). To calculate cell numbers, live GFP-cells were normalized to calibration beads.

Mouse xenografts. $1 \times 10^6$ H929 Luc+ cells and $1 \times 10^6$ mouse BM stromal cells were resuspended in 100 μl MATRIGEL®, diluted with RPMI (1:1), and injected subcutaneously into 16-week-old male NSG mice. After 4 days, treatment with BTZ (0.5 mg/kg i.p. twice weekly) and IRX (10 mg/kg i.p. daily) was initiated. Tumor burden was assessed by bioluminescence using the In Vivo Imaging System (PerkinElmer). For imaging, mice were exposed to 120 mg/kg D-luciferin via intraperitoneal injection 10-5 min before imaging and were anesthetized using isoflurane. Images were analyzed with Living Image Software, version 2.5 (PerkinElmer), and data were quantified as photons/second.

For the systemic MM model, $2 \times 10^6$ Luc+/GFP+ H929 cells were injected via the tail vein into 16-week-old male NSG mice. After engraftment, as determined by an exponential increase in bioluminescence, mice were treated with BTZ (0.5 mg/kg i.p.) twice weekly and with IRX (10 mg/kg) once daily. Tumor burden was assessed by bioluminescence, as above.

Statistics. First evaluated was whether the treatment groups were different from the controls using 1-way ANOVA. If the ANOVA test yielded a statistically significant result, then the difference between the control group and each treatment group was evaluated, with the P values adjusted for multiple comparisons using Dunnett's test. For experiments in which only 2 sets of data were analyzed, statistical significance was evaluated using an unpaired, 2-tailed Student's t test. Pearson's R value for correlation and P values were calculated using GraphPad Prism 7 (GraphPad Software).

Results

The BM microenvironment (also called "niche") limits PC differentiation by modulating retinoid signaling. A population of MM progenitors, phenotypically similar to B cells, is intrinsically resistant to BTZ and contributes to MRD and relapse. To investigate whether the BM niche plays a role in determining the phenotype of MM cells, the mRNA expression of B cell and PC markers in MM H929 cell lines (FIG. 3A-D) and MM CD138+ primary cells (FIG. 3E-H) was analyzed following co-culture with mouse BM stroma using human-specific primers. B cell lymphoma 6 (BCL6), a transcriptional repressor that promotes self-renewal of germinal center B cells and prevents PC differentiation, was upregulated in the presence of BM stromal cells (FIG. 3A, 3E). In contrast, co-culture of MM cells with BM stroma decreased the mRNA expression of B lymphocyte-induced maturation protein 1 (BLIMP1) and spliced X box-binding protein 1 (XBP1s) (FIG. 3B, C, F, G), which are critical mediators of PC differentiation. Similarly, C/EBP homologous protein (CHOP), a key component of the UPR pathway, was downregulated in the presence of BM stromal cells (FIG. 3D, H).

The BM niche regulates hematopoietic stem cell (HSC) differentiation by expressing the retinoid-inactivating enzyme CYP26. CYP26 enzymes were highly expressed in BM mesenchymal cells, while their expression was barely detectable in MM cells. Since retinoid signaling promotes PC differentiation and potentiates Ig secretion, it was determined whether stromal CYP26 is responsible for inducing a B cell phenotype in MM cells. To this end, co-culture conditions were treated with the CYP26 inhibitor R115866 (R115) or the CYP26-resistant RA receptor α-selective (RARα-selective) retinoid IRX5183 (IRX). Incubation of stroma co-cultures with either R115 or IRX restored all markers to levels comparable to those of liquid control conditions (FIG. 3A-H). Moreover, treatment of MM cells with the pan-RAR antagonist AGN194310 (AGN) mimicked the changes induced by BM stromal cells (FIG. 3A-H), limiting PC differentiation.

Expression of CD138 is a hallmark of normal PC differentiation as well MM PCs. Consistent with mRNA levels of PC markers, surface CD138 expression was markedly decreased by co-culture with BM stromal cells or incubation with AGN. Incubation of BM stromal cell co-cultures with R115 or IRX restored CD138 expression in MM cells. R115 did not significantly affect the expression of differentiation markers in liquid conditions by quantitative reverse transcription-PCR (qRT-PCR) or flow cytometry, while IRX induced comparable changes, irrespective of the presence or absence of BM stroma. Taken together, these data suggest that retinoid signaling promotes PC differentiation of MM cells and that this process is blocked by stromal CYP26-mediated metabolism of RA.

Figure 4A:
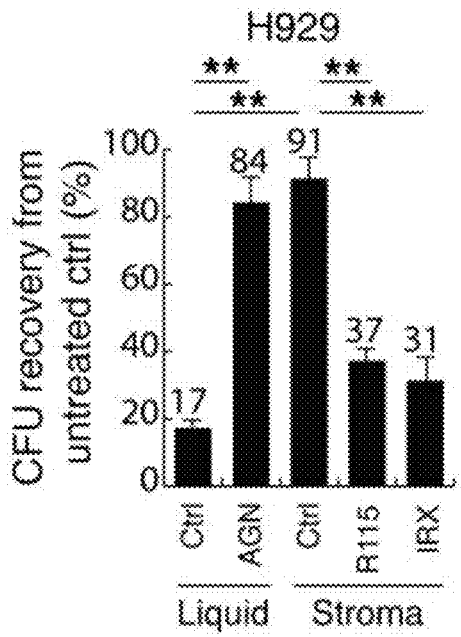
FIG. 4A-B depicts the clonogenic recovery (CFU) of H929 cells (FIG. 4A) or cellular recovery of primary CD138+ MM cells from 3 different patient samples (FIG. 4B). MM cells were treated with bortezomib (BTZ; 2.5 nM) for 48 hours after being incubated for 5 days either in the absence of stroma (Liquid), with or without the pan-RAR inhibitor AGN (1 μM), or in the presence of BM mesenchymal cells (Stroma), with or without the CYP26 inhibitor R115 (1 μM) or the CYP26-resistant retinoid IRX (1 μM). Clonogenic or cellular recovery was normalized to each condition in the absence of BTZ.
Figure 4B:
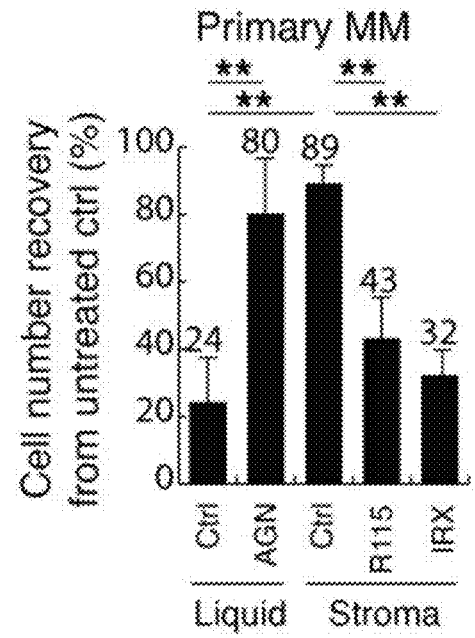

A RA-low microenvironment induces BTZ resistance. To determine whether decreased retinoid signaling contributes to BTZ resistance within the BM niche, MM cell lines and MM CD138+ primary cells were incubated with BM stroma for 5 days, followed by BTZ treatment. In the absence of BM stroma (liquid), MM cells were highly sensitive to BTZ (FIG. 4A-B). However, incubation with BM stroma induced BTZ resistance, which was overcome by CYP26 inhibition via R115 or by the CYP26-resistant retinoid IRX. Moreover, treatment of MM cells with the pan-RAR antagonist AGN mimicked the changes induced by BM stromal cells (FIG. 5), decreasing BTZ sensitivity.

Figure 5:
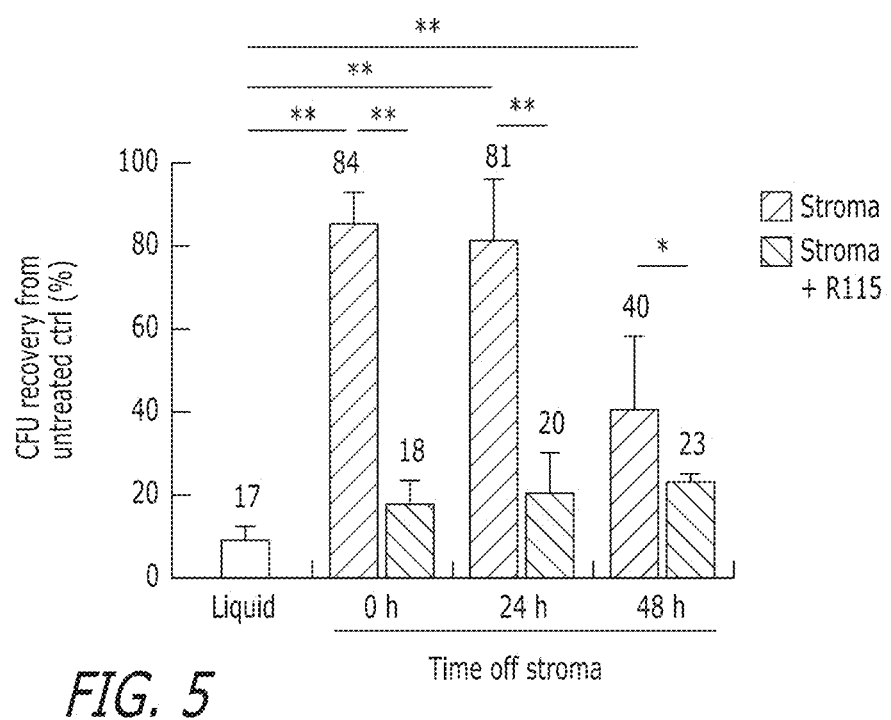
FIG. 5 depicts clonogenic recovery of H929 cells treated with BTZ (2.5 nM). MM cells were incubated for 5 days in the absence (Liquid) or presence of BM mesenchymal cells (Stroma), with or without R115 (1 μM). Following this preincubation, H929 cells were separated from BM stroma, cultured in fresh media for 0 to 48 hours, and then treated with BTZ (2.5 nM) for 48 hours. Clonogenic recovery was normalized to each condition in the absence of BTZ.

Strategies to overcome microenvironment-dependent chemoprotection have focused on mobilization of cancer cells from the BM niche into the peripheral circulation. It was analyzed whether the change in phenotype and subsequent BTZ resistance of MM cells were lost upon separation from the BM stroma, a process that mimics mobilization. To this end, H929 cells were separated from BM mesenchymal cells following a 5-day stroma co-culture, incubated in fresh media (RPMI with 10% FBS) for 0 to 48 hr, and then treated with BTZ. Interestingly, MM cells remained partially resistant to BTZ for up to 48 hr following detachment from stroma (FIG. 5). Moreover, treatment of the co-culture conditions with R115 prevented the development of a BTZ-resistant phenotype (FIG. 5). Thus, microenvironment-dependent BTZ resistance induced by the change in MM cell phenotype may not immediately be reversed by tumor mobilization.

Figure 6:
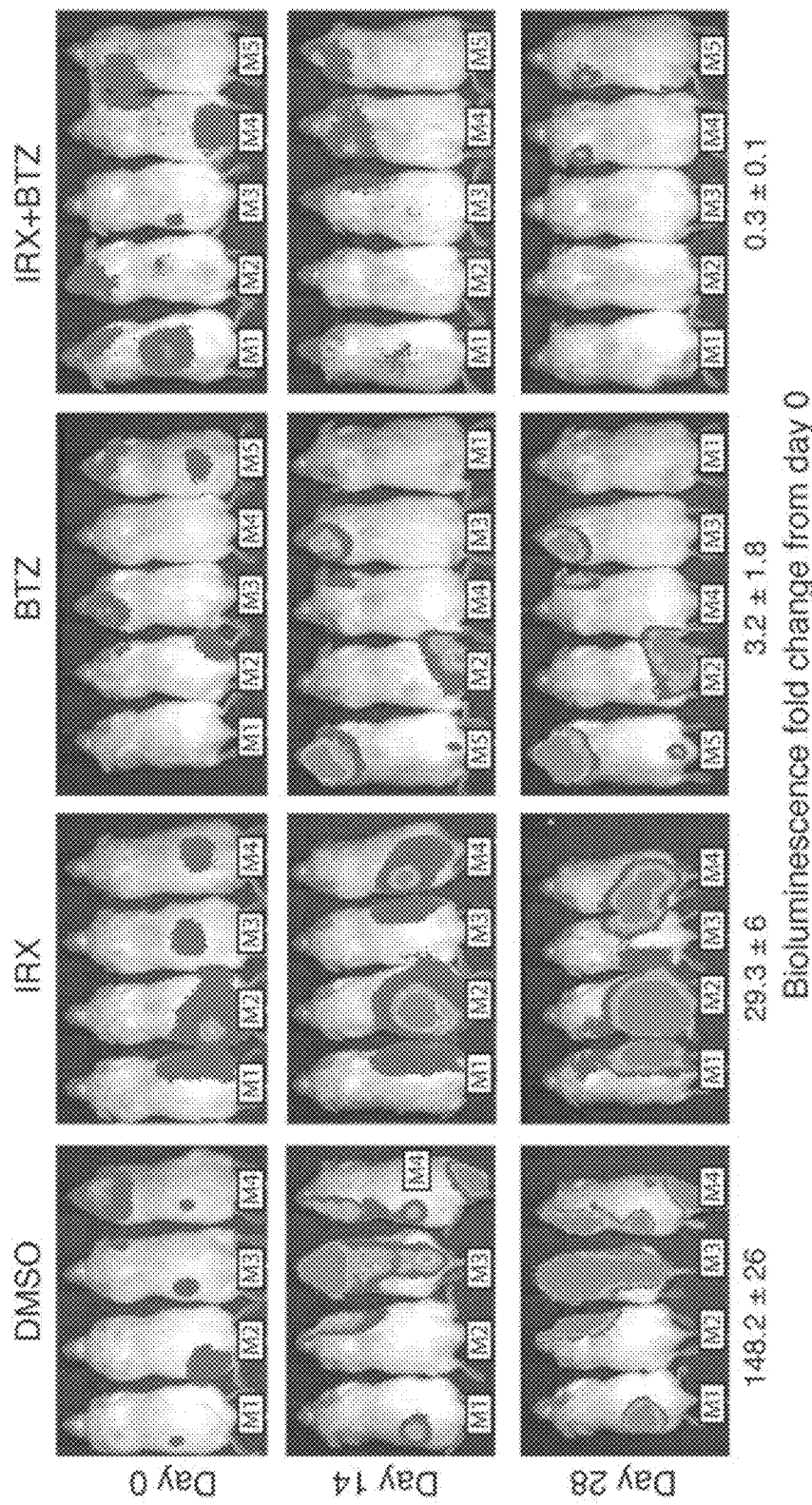
FIG. 6 depicts bioluminescent images of systemic MM xenografts. Following engraftment of H929 Luc+ cells, mice were treated with IRX (n=4), BTZ (n=5), or a combination of both (n=5) for 4 weeks. Data represent the mean±SEM of the fold change in bioluminescence (photons/second) from day 0.

To test whether retinoids can enhance BTZ activity in MM, a systemic MM xenograft was developed by injecting $2\times10^6$ H929 luciferase+ (Luc+) cells via the tail vein of non-obese, diabetic, severe combined immunodeficiency IL-2 receptor γ-KO (NSG) mice. The animals were randomized to receive IRX, BTZ, or a combination of both, and disease burden was followed weekly by bioluminescence imaging (FIG. 6). Mice treated with BTZ showed decreased tumor growth compared with untreated controls; however, some MM cells remained resistant to BTZ, as demonstrated by the continued increase in bioluminescence. Similarly, mice treated with IRX monotherapy showed a decrease in tumor burden compared with untreated mice. Most important, IRX sensitized MM cells to BTZ, leading to a significant ($P<0.01$) decrease in disease burden. Collectively, these data suggest that an RA-low microenvironment created by stromal CYP26 induces a BTZ-resistant phenotype, which is maintained even after displacement from the BM niche.

Figures 7A, 7B, 7C:
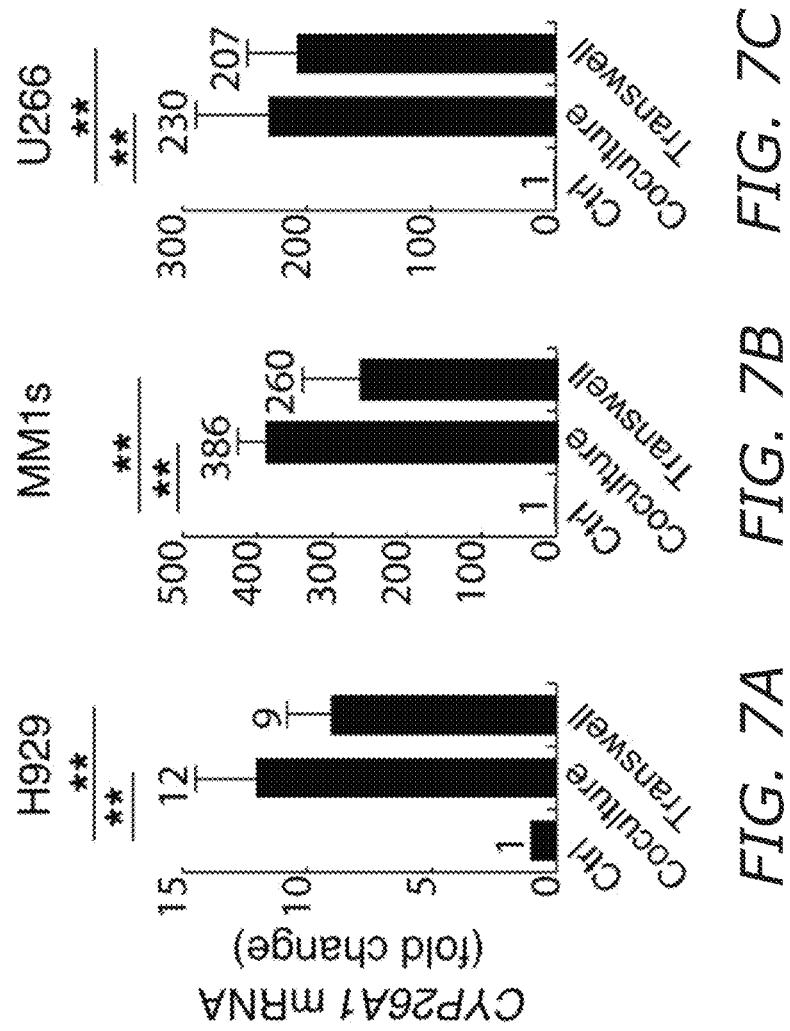
FIG. 7A-C depicts the effects of MM cells on the expression of CYP26A1 in BM stroma. Relative quantification of CYP26A1 mRNA in human BM mesenchymal cells incubated for 24 hours either in the absence (Ctrl) or presence (Coculture or Transwell) of MM cells (H929 [FIG. 7A], MM.1S [FIG. 7B], U266 [FIG. 7C]). Expression in untreated BM stroma (Ctrl) was arbitrarily set at 1.

MM cells induce stromal CYP26. Recent studies have demonstrated the existence of a bi-directional crosstalk, in which not only stromal cells provide a protective microenvironment, but also cancer cells actively adapt and build a reinforced niche. Thus, it was determined whether MM cells reinforce a protective microenvironment by strengthening the ability of BM stroma to inactivate retinoids. Stromal CYP26 expression was analyzed by qRT-PCR in BM mesenchymal cells following a 24-hr coculture with MM cells. The isoenzyme CYP26A1 was highly upregulated by all 3 MM cell lines tested (FIG. 7A-C). In contrast, the isoenzyme CYP26B1 showed little to no changes in mRNA levels. Conditioned media derived from MM cells also upregulated CYP26A1 in BM stromal cells, although to a lesser extent. This could be explained by the presence of physical interactions in coculture experiments, or the lack of continuous production of soluble ligands by MM cells in conditioned media experiments. Consistent with the latter, stromal CYP26A1 was highly upregulated when MM and BM stromal cells were separated by a Transwell that prevented physical contact but allowed the diffusion of soluble factors (FIG. 7A-C).

MM cells produce a variety of soluble factors including cytokines (IL-1, IL-3, IL-6, TNF-α) as well as Hedgehog ligands such as sonic hedgehog (SHH), which could impact the BM stromal compartment. Therefore, it was determined whether any of these factors was responsible for the observed upregulation of CYP26A1 on BM stromal cells. Of the soluble factors tested, only SHH produced a sustained overexpression of CYP26A1, while IL-1, IL-3, IL-6, and TNF-α had no significant effects. Whereas SHH is expressed by BM stromal cells and thus may be able to activate the Hedgehog pathway in an autocrine manner, its expression was considerably higher in MM cells compared with that detected in BM stroma, suggesting that paracrine activation may play a dominant role. Consistent with this, there was a statistically significant correlation between the mRNA levels of SHH in MM cells and activation of stromal Hedgehog signaling as determined by protein patched homolog 1 (PTCH1) expression. Moreover, activation of stromal Hedgehog significantly correlated with CYP26A1 upregulation. Specifically, MM.1S cells with the highest expression of SHH also induced the highest expression of both PTCH1 and CY26A1 in stromal cells. SHH has a half-life of less than 1 hr, which may explain the reduced effect of MM-conditioned media on stromal CYP26A1 expression compared with that observed in coculture and Transwell experiments.

Figures 8A, 8B, 8C:
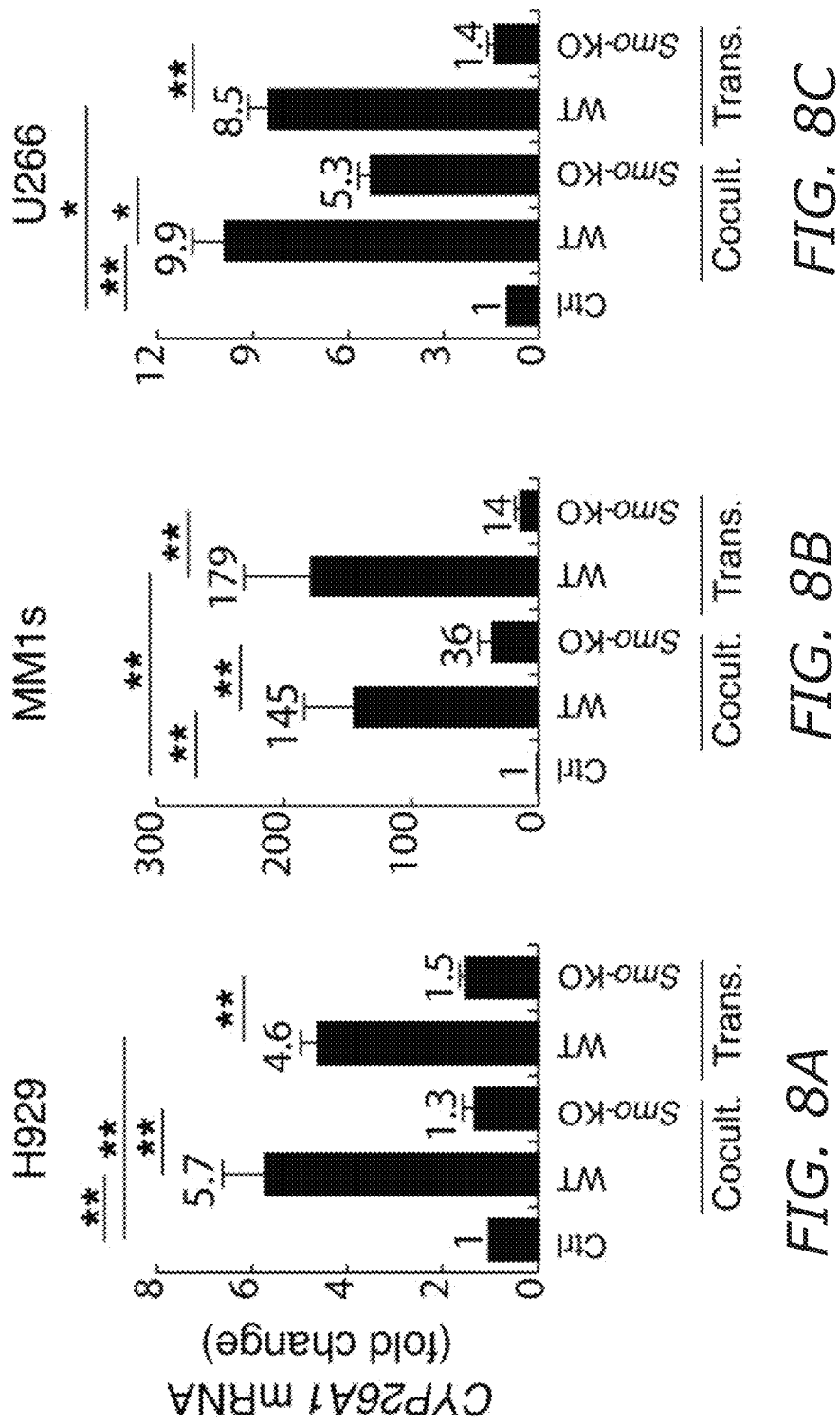
FIG. 8A-C depicts the relative quantification of CYP26A1 mRNA in mouse wild type (WT) or Smo-KO BM stroma incubated for 24 hr in the absence (Ctrl) or presence (Coculture or Transwell) of MM cells (H292, MM.1S, U266). Expression in untreated WT or Smo-KO stroma was arbitrarily set at 1 for the respective treated conditions. Data represent the mean±SEM of 3 independent experiments. *$P \leq 0.05$ and **$P \leq 0.01$, by unpaired, 2-tailed Student's t test.

To confirm the role of paracrine Hedgehog on this interaction, smoothened (Smo), a membrane receptor that transduces SHH signaling, was knocked out at the genomic level in the mesenchymal compartment. For this, BM mesenchymal cells derived from $Smo^{fl/fl}$ mice were transduced with a retroviral vector encoding Cre recombinase (Smo-KO stroma). Mouse $Smo^{fl/fl}$ stromal cells transduced with an empty retroviral vector were used as a control (WT stroma). The transduced BM stromal cells were cocultured with MM cells for 24 hr. As expected, Smo-KO stroma had a decreased ability to upregulate Cyp26a1 in response to MM cells compared with WT stroma (FIG. 8A-C). Similarly, the SMO inhibitor cyclopamine partially overcame stromal Cyp26a1 upregulation by MM cells. These data suggest that MM cells modulate stromal CYP26 expression at least in part via paracrine SHH.

Paracrine Hedgehog produced by MM cells reinforces a protective microenvironment. Given the observations that stromal CYP26 activity may be responsible for BTZ resistance in MM cells, it was assessed whether paracrine Hedgehog secreted by MM cells reinforces a chemoprotective niche by regulating retinoid metabolism. It was first investigated whether modulation of Hedgehog signaling paralleled the retinoid-dependent phenotypes observed previously. Disruption of paracrine Hedgehog signaling in Smo-KO stroma cocultures partially restored PC differentiation (downregulation of BCL6 and upregulation of BLIMP1, XBP1, and CHOP) in H929 (FIG. 11A-D) and primary CD138+ MM cells (data not shown). Surface expression of CD138 was also restored in the presence of Smo-KO stroma. As expected, these findings were associated with an increased sensitivity to BTZ of MM cells treated in the presence of Smo-KO stroma compared with WT stroma.

To demonstrate that paracrine Hedgehog indeed induces a BTZ-resistant phenotype by increasing the ability of BM stroma to inactivate retinoids, Cyp26a1 expression in Smo-KO stroma was rescued via lentivirus-mediated gene transfer (pBABE-Cyp26a1) in order to achieve comparable CYP26A1 levels in WT (WT-Cyp26a1) and Smo-KO (Smo-KO-Cyp26a1) stromal cells. If the role of paracrine Hedgehog was independent of retinoid signaling, the relative inability of Smo-KO stroma to induce a B cell phenotype and BTZ resistance should have persisted even after Cyp26a1 upregulation. However, Cyp26a1 overexpression rescued the ability of Smo-KO stroma to induce a B cell phenotype and restored the expression of differentiation markers and BTZ resistance to levels comparable to those detected in WT and WT-Cyp26a1 stroma coculture conditions. This finding is consistent with the hypothesis that paracrine Hedgehog reinforces a protective niche via Cyp26a1 upregulation.

Figure 9:
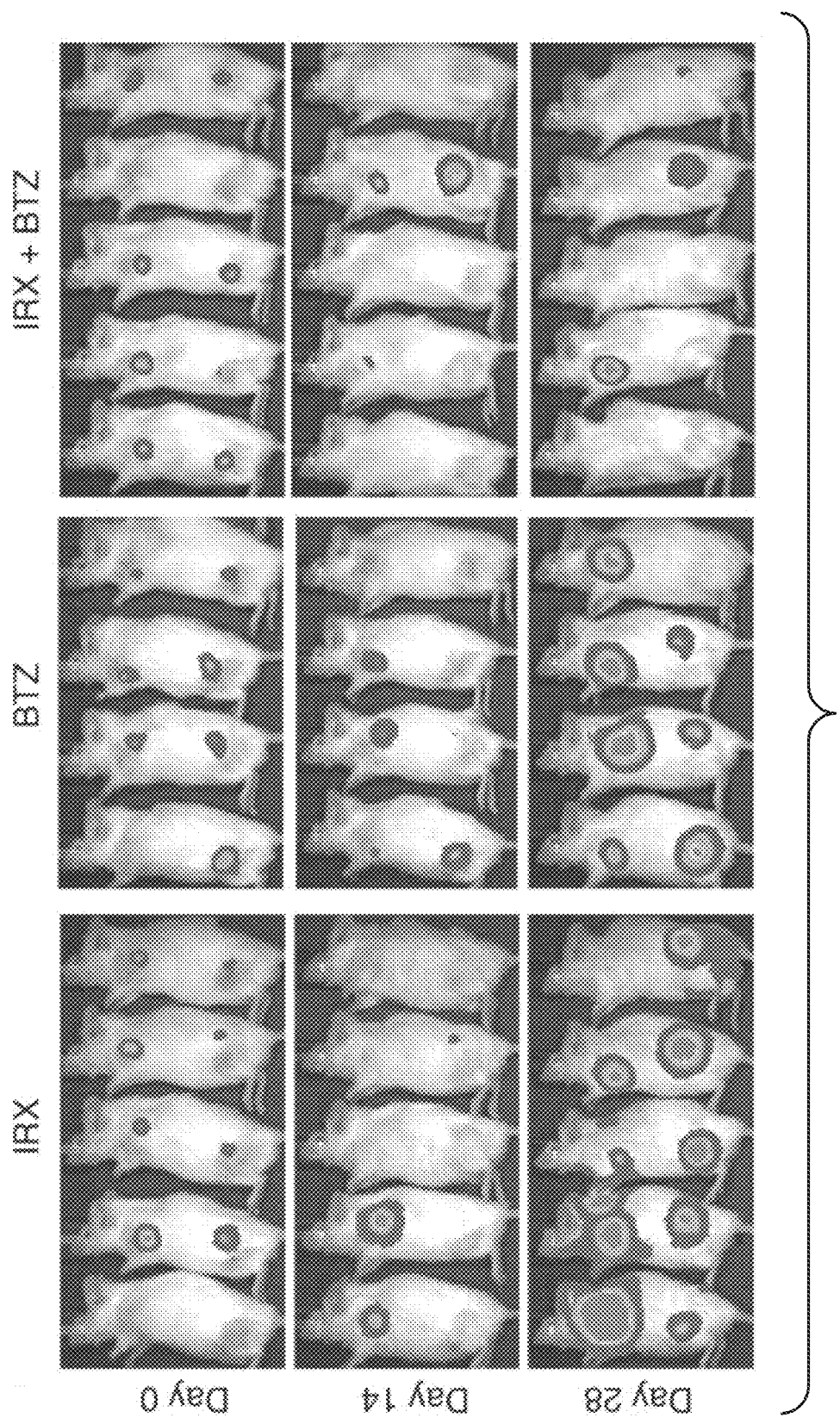
FIG. 9 depicts bioluminescent images of mice showing tumor burden during 4 weeks of treatment with IRX (10 mg/kg), BTZ (0.5 mg/kg), or the combination. Anterior tumors consisted of a combination of MM.1S luciferase$^+$ cells and Smo$^{Fl/Fl}$ BM stroma cells transduced with a control vector (WT BM stroma). Posterior tumors consisted of a combination of MM.1S luciferase$^+$ cells and Smo$^{Fl/Fl}$ BM stroma cells transduced with Cre-recombinase (Smo KO BM stroma).
Figure 10:
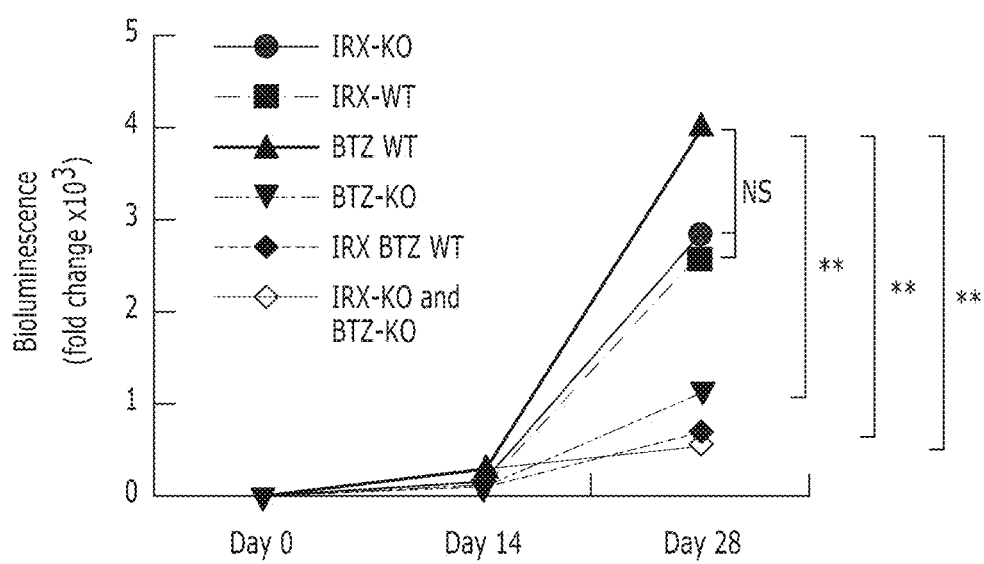
FIG. 10 depicts the fold change in bioluminescence (photons/second) of tumors during 4 weeks of treatment. The change in bioluminescence for each tumor at day 1 was normalized to the change in bioluminescence at day 14 and at the end of treatment (day 28).
Figures 11A, 11B, 11C, 11D:
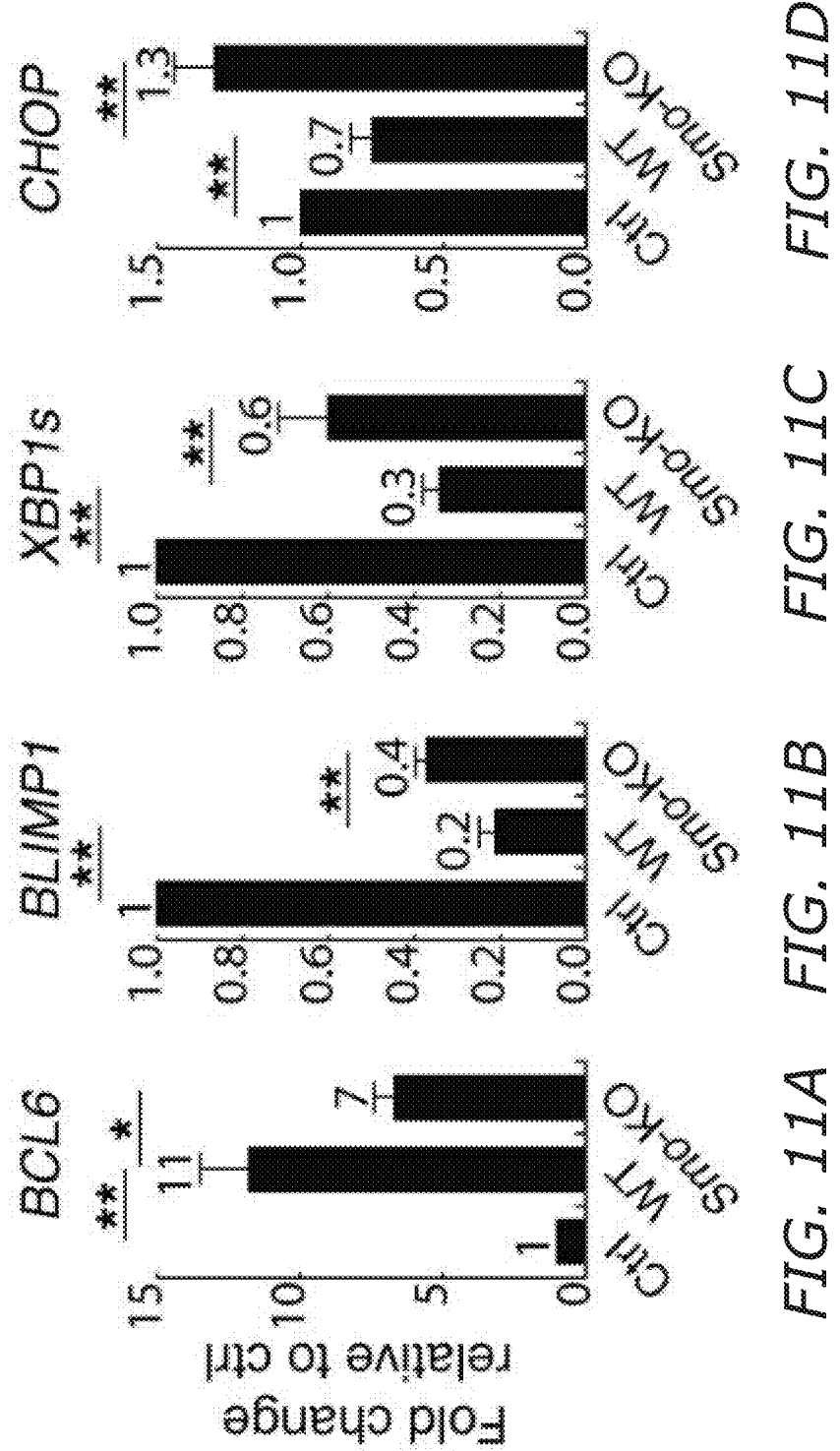
FIG. 11A-D depicts the relative quantification of BCL6 (B cell marker)(FIG. 11A), BLIMP (FIG. 11B), XBP1s (FIG. 11C), and CHOP (FIG. 11D), (PC markers) in H929 cells from 3 different patient samples incubated for 5 days either in the absence of stroma (Ctrl) or co-cultured with WT or Smo-KO stromal cells. Expression in untreated liquid conditions was set at 1. Data represent the mean±SEM. *$P \leq 0.05$ and **$P \leq 0.01$, by repeated-measures 1-way ANOVA to determine statistical significance between treatment groups; P values were corrected for multiple comparisons using Dunnett's test.
Figure 12A:
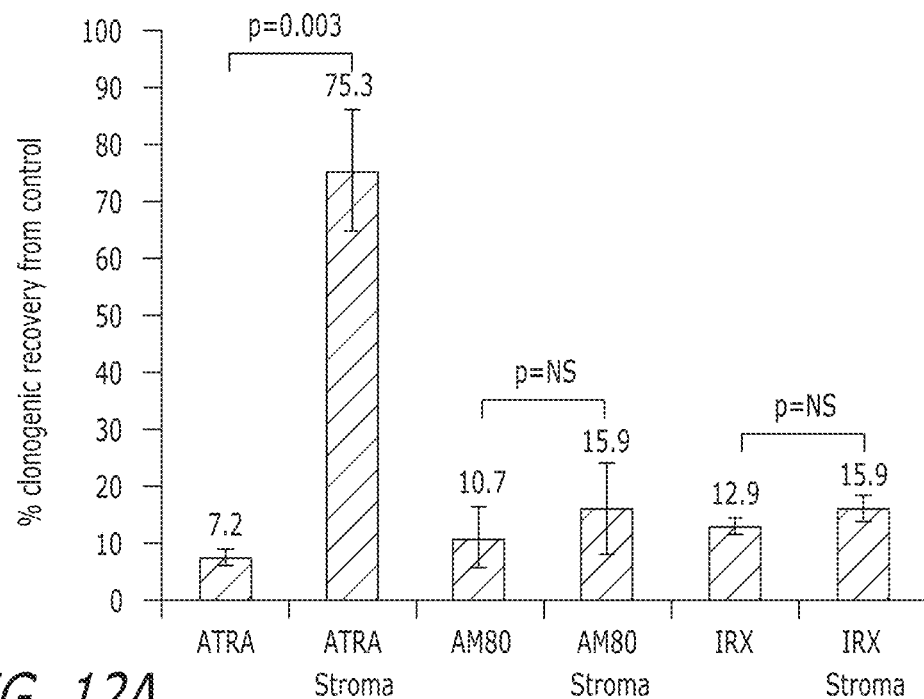
FIG. 12A-C depicts stroma blockage of ATRA-mediated, but not AM80- or IRX5183-induced, differentiation and elimination of AML.
Figure 12B:
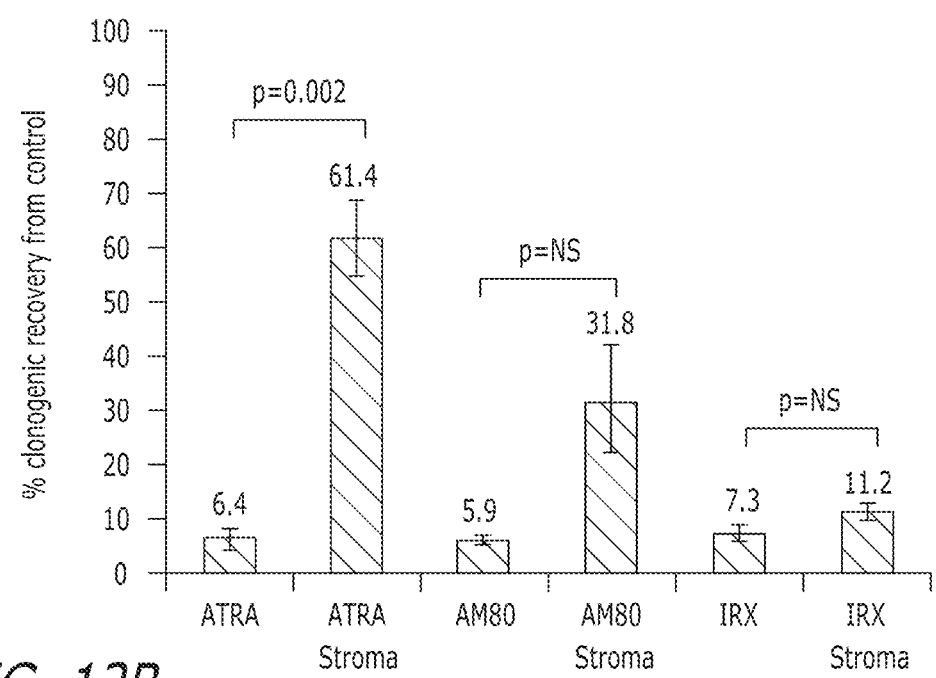
Figure 12C:
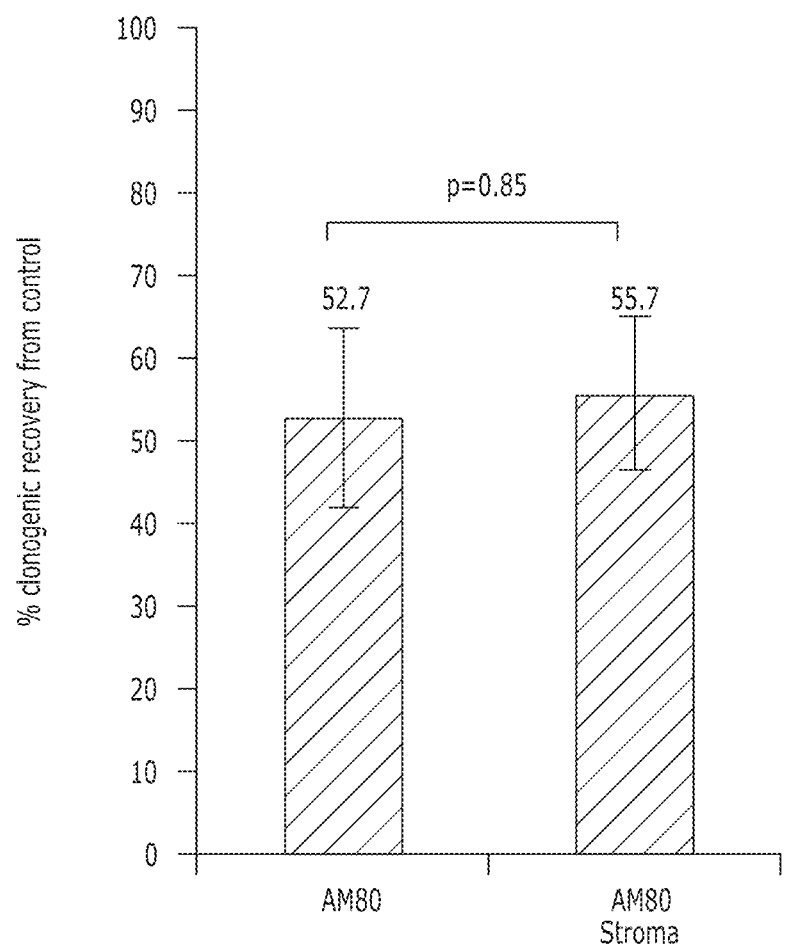

To study to what extent an RA-low environment created by the BM stroma and enhanced by MM cells via paracrine Hedgehog signaling contributes to BTZ resistance, a xenograft model of MM-niche interactions was developed. Each mouse carried 2 subcutaneous tumors consisting of H929 Luc+ cells and either WT (anterior tumors) or Smo-KO stroma (posterior tumors). Mice were treated with IRX (10 mg/kg i.p. daily), BTZ (0.5 mg/kg i.p. twice weekly), or a combination of both. The growth of tumors bearing WT or Smo-KO stroma was not different in untreated or IRX-treated groups (FIGS. 9 and 10). Consistent with in vitro data, tumors with WT stroma were refractory to BTZ treatment, as determined by an exponential increase in bioluminescence, while tumors carrying Smo-KO stroma showed a significant response (FIG. 8). Moreover, the combination of IRX and BTZ resulted in a significant and equivalent response, regardless of the phenotype of the stromal compartment (FIG. 10). While some tumors in the treatment group receiving combined IRX and BTZ appeared to have regressed completely, even after anatomical study, this was not the case for all the mice in this group. Flow cytometric analyses of the tumors after treatment revealed no differences in the in vivo growth of WT or Smo-KO stroma. Taken together, these data suggest that paracrine Hedgehog secreted by MM cells modulates retinoid signaling and BTZ sensitivity in the BM niche via CYP26A1 upregulation.

Given their high secretion of Ig, PCs are particularly sensitive to proteasome inhibition, and this accounts for the high remission rates achieved in MM patients treated with this family of drugs. Nonetheless, BTZ has failed to achieve a cure. A population of MM cells, phenotypically similar to B cells, survive BTZ treatment and are able to differentiate into PCs and recapitulate the original disease. Despite efficient elimination of MM PCs, these MM B cells survive BTZ treatment and become the predominant cell population during MRD. Consequently, new therapeutic strategies targeting MM B cells are required. A retinoid-low microenvironment created by stromal CYP26 maintained an immature, BTZ-resistant phenotype in MM. Thus, these data reveal a therapeutic opportunity to overcome BTZ resistance in the MM microenvironment using CYP26-resistant retinoids.

Despite being extensively studied in many hematological malignancies, the use of retinoids as differentiation therapy has proved beneficial only in patients with acute promyelocytic leukemia (APL). CYP26 expression by BM stromal cells may explain the lack of a clinical benefit of natural retinoids, despite their in vitro activity. Recent studies have highlighted the efficacy of CYP-resistant synthetic retinoids in differentiating cancer cells and sensitizing them to targeted therapy. For instance, AM80 differentiates FMS-like tyrosine kinase 3/internal tandem duplication (FLT3/ITD) acute myeloid leukemia (AML) cells and increase their sensitivity to FLT3 inhibitors. Similarly, synthetic retinoids reverse a stem cell phenotype in BCR-ABL1+ leukemic lymphoblasts and substantially increase their responsiveness to tyrosine kinase inhibitor (TKI) therapy in vivo. Such strategies to bypass stromal CYP26 could expand the clinical effectiveness of retinoid therapy.

MM cells utilize physical contacts to maintain drug resistance and survive within the BM niche. Thus, therapeutic strategies to overcome stromal chemoprotection have focused on mobilization of malignant cells from the BM niche by targeting adhesion molecules or chemokines such as CXCR4. MM cells exposed to a retinoid-low microenvironment acquire a BTZ-resistant phenotype that is maintained even after these cells are displaced from their niche. Initial clinical studies have shown improved response rates in relapse/refractory patients receiving the CXCR4 inhibitor plerixafor in combination with BTZ; however, this data suggest that such mobilization approaches may be insufficient to eliminate MM B cells.

Recent studies have demonstrated the existence of a bidirectional communication, in which not only stromal cells provide a chemoprotective niche, but also cancer cells actively shape and reinforce their microenvironment. The role of paracrine Hedgehog has been studied extensively in solid malignancies. In this system, ligands secreted by cancer cells activate the Hedgehog pathway in neighboring stromal cells, enhancing their chemoprotective properties via incompletely understood mechanisms. This data suggest that paracrine Hedgehog may work at least in part by increasing the ability of stroma to inactivate retinoids through upregulation of CYP26 and thus to maintain a BTZ-resistant phenotype in MM. Interestingly, CYP26 upregulation is associated with an "activated stromal subtype" and a significantly worse prognosis in patients with pancreatic cancer, a disease in which paracrine Hedgehog signaling is well established. The extent to which Hedgehog ligands produced by cancer cells contribute to this "activated" stromal phenotype and high CYP26 levels is unknown. Moreover, BM mesenchymal cells migrate and become a relevant cell population in the stromal compartment of these tumors.

The endosteal region is the primary niche of MM, AML, and micrometastatic disease from solid tumors. Within the osteoblastic region, these cancer cells maintain a quiescent, stem cell phenotype and are protected from chemotherapy-induced apoptosis. It is likely that these cancer cells rely on the same cues from the BM microenvironment as normal hematopoietic stem cells do to survive chemotherapy and perpetuate the disease. The BM microenvironment protected MM and AML cells by directly inactivating various chemotherapy agents via expression of CYP3A4 and other detoxifying enzymes. Another potential mechanism of microenvironment-mediated drug resistance is now demonstrated: creation of a retinoid-low niche that maintains a drug-resistant B cell phenotype. A CYP26-resistant retinoid (IRX5183) potentiated the activity of BTZ against MM in the BM niche provides a therapeutic opportunity to bypass this mechanism of resistance.

Example 6

Phase I/II Clinical Study of IRX5183 in Acute Myeloid Leukemia

Acute myeloid leukemia (AML) is successfully treated in only 30-40% of younger patients and very few older patients with standard chemotherapy regimens. Given the clinical activity of all-trans retinoic acid (ATRA; retinoic acid, RA) in acute promyelocytic leukemia (APL), ATRA was considered an attractive therapeutic strategy for other AML sub-types. APL, and most non-APL AMLs undergo terminal differentiation and are therefore successfully treated by ATRA in vitro. However, ATRA has not proven effective in non-APL AMLs in clinical trials.

Retinoic acid (RA) plays a significant role in the differentiation of hematopoietic stem cells (HSCs). The cytochrome P450 enzyme CYP26, expressed in bone marrow (BM) stromal cells, inactivates RA, thereby limiting differentiation of HSCs. Several AML cell lines, both APL and non-APL, are sensitive to RA-induced differentiation, but this effect was abrogated in the presence of BM stroma. Thus, it may be useful to treat AML with a retinoid that is resistant to metabolism by the CYP26 pathway. IRX5183 is a RARα selective agonist which is resistant to CYP26 metabolism. Use of IRX5183 in AML provides a novel targeted approach to this disease, which has the potential to change the prognosis of this and other hematologic malignancies. Thus, a phase I/II clinical trial will be conducted of IRX5183 in relapsed/refractory AML.

Study Objectives
Dose escalation phase primary objectives:
Evaluate safety and toxicity associated with administration of IRX5183 in patients with relapsed and refractory AML by determining the dose limiting toxicities (DLT) and maximally-tolerated dose (MTD).
Determine pharmacokinetic (PK) parameters of IRX5183 in the peripheral blood.
Dose escalation phase secondary objectives:
Determine the PK parameters of IRX5183 in the bone marrow.
Define differentiation profiles associated with IRX5183, BM cellular retinoid concentrations, blast counts, and cytogenetics at different dose levels.
Dose expansion phase primary objectives:
Define differentiation markers, BM retinoid concentrations, blast counts, and cytogenetics in AML patients at the optimal dose level.
Obtain preliminary efficacy data of IRX5183 in terms of complete response (CR), partial response (PR), and hematological improvement (HI) in both cohorts of patients.

Dose expansion phase secondary objectives:
Define toxicity profiles of IRX5183 at the optimal dose in both patient cohorts.
Obtain data on correlations between IRX5183-induced differentiation and toxicity and clinical responses.
Eligibility criteria—dose escalation/determination.
Patients must be able to understand and voluntarily sign an informed consent form.
Age 18-70 years at the time of signing the informed consent.
Able to adhere to the study visit schedule and other protocol requirements.
Life expectancy of greater than 6 months.
Must have pathologically confirmed AML with one or two prior courses of induction chemotherapy or hypomethylating agent therapy or relapsed after complete remission, before or after allogeneic bone marrow transplant, AND no plans for further intensive chemotherapy.
Patients must not have received any other treatment for their disease (aside from hydroxyurea for control of blast count in AML patients), including hematopoietic growth factors, within three weeks of beginning the trial, and should have recovered from all toxicities of prior therapy (to grade 0 or 1).
ECOG performance status of ≤2 at study entry, or Karnofsky ≥60%.
Laboratory test results within these ranges:
Calculated creatinine clearance by MDRD (CrCL) >50 ml/min/1.73 squared meter
Total bilirubin ≤2.0 mg/dL unless due to Gilbert's syndrome, hemolysis, or ineffective hematopoiesis AST (SGOT) and ALT (SGPT) ≤3×ULN
Females of childbearing potential must have negative pregnancy test.
Patients must have no clinical evidence of CNS or pulmonary leukostasis, disseminated intravascular coagulation, or CNS leukemia.
Patients must have no serious or uncontrolled medical conditions.
Eligibility criteria—dose expansion. This phase will follow the noted eligibility criteria above, including pathologically confirmed chronic myelomonocytic leukemia (CMML) with high risk features at the time of referral as defined by:
INT-2 or high IPSS score
CMML with ≥5% marrow blasts, or RBC or platelet transfusion-dependency, abnormal karyotype, or proliferative features
Treatment Plan
For the dose escalating phase, IRX5183 is administered orally in daily doses continually in 28 day cycles until toxicity or disease progression. Bone marrow testing during each of the first 4 cycles determines marrow status and response. The starting dose (DL1) of single agent IRX5183 is 30 mg/m$^2$/day, and the individual dosing levels are noted below:

| Dose level (DL) | Daily dose (mg/m$^2$) |
| --- | --- |
| DL(−1) | 15 |
| DL1 | 30 |
| DL2 | 45 |
| DL3 | 60 |
| DL4 | 75 |

The phase-expansion part of the study uses the optimal dose identified in the phase-escalation part of the study and will recruit 26 patients.

Dose levels are explored according to a traditional 3+3 design, with an aim to enroll 3 subjects at a time to determine the toxicity profile of IRX5183 in AML patients. If none of the three patients receiving DL1 experiences a DLT, another three patients will be treated at the next higher dose level. However, if one of the first three patients experiences a DLT, three more patients will be treated at the same dose level. The dose escalation will continue until at least two patients among a cohort of 3-6 patients experience DLTs. If two or more patients experience DLT on DL1, the next patient will be recruited to DL(-1). The MTD of single agent IRX5183 will be the highest dose at which 0 or 1 DLT are seen in a cohort of six subjects.

For the phase 2 dose expansion cohort, patients with AML are continued to be enrolled at the MTD, with goal of enrolling 26 patients (inclusive of patients treated at the MTD in first phase of the trial). Patients continue on single agent IRX5183 until they experience toxicity or disease progression. If patients achieve a complete remission, they have the option to consolidate with transplant, chemotherapy, and/or continue on maintenance IRX5183. If patients achieve a partial response or hematologic improvement they have the option to obtain salvage therapy in combination with IRX5183.

Pharmacokinetics Analyses. Plasma concentrations of IRX5183 are evaluated for the escalation and expansion phases, targeting safe and effective retinoid levels by pharmacokinetics using LCM-MS (liquid chromatography-mass spectroscopy tandem). Targeting peak levels of 1 pM should avoid systemic toxicity, while presumably preserving local BM niche retinoid levels. The plasma concentration of IRX5183 is obtained using a single 2 mL blood sample, pre-dose on day 14. Samples are shipped to and analyzed by the designated analytical laboratory.

Pharmacodynamics Analyses. In addition to assessing standard clinical response criteria, BM cellular (normal HSCs and LSCs) concentrations, peripheral blood and bone marrow blast counts, markers of differentiation, apoptosis, and clonogenic growth are determined. A bone marrow aspirate and biopsy are obtained at baseline, on day 14, and at the end each of the first 4 cycles of therapy. Differentiation is assessed using flow cytometry, comparing expression of differentiation markers on CD45 positive cells and ALDHint LSCs on day 14 marrow versus baseline. FISH analysis is also conducted after each cycle for patients with baseline abnormalities to determine if leukemic clone still present on day 14.

Expected Outcomes

Patients receiving RARα selective agonist are monitored for response criteria based on hematological parameters including complete blood counts and percentage of leukemia blasts in the peripheral blood and in the bone marrow. Patients with improved neutrophil count, decreased transfusion requirements of red blood cells and platelets together with decreased percentage of blasts in the bone marrow and induction of differentiation and apoptosis of these malignant blasts are deemed responsive to therapy. Quality of life parameters such as pain, performance status and participation in activity of daily living and instrumental activities of daily living are assessed to evaluate the impact of this therapy on study patients. Use of this RARα selective agonist is expected to improve hematological and quality of life parameters in patients with AML and solid malignancies. In addition, the use of the RARα agonist which is CYP26 resistant may result in differentiation and thus elimination of minimal residual disease in the bone marrow of these patients.

Example 7

Clinical Study of IRX5183+CAR-Modified Immune Cells in Acute Myeloid Leukemia

Eligibility criteria are the same as in Example 6.

Treatment Plan

The study uses the optimal dose of IRX5183 identified in the phase-escalation study (Example 6) and includes two separate arms; one for patients receiving CAR-modified immune cells alone (Group 1) and another for patient receiving both IRX5183 and CAR-modified immune cells (Group 2), and each of these two arms will recruit 26 patients.

All patients are administered fludarabine at 25 mg/m$^2$ intravenously on days D-5 to D-3 and 900 mg/m$^2$ cyclophosphamide on day D-3.

Group 1 patients receive autologous CD33-CAR-T cells as disclosed and prepared in Minagawa et al. (PLoS One 12:e0172640, 2017) and administered intravenously at a dose of 5×10$^6$ cells/kg of patient body weight in a single bolus dose.

Group 2 patients are treated with daily IRX5183 for 30 days prior to initiating autologous CD33-CAR-T cell therapy (D-30) and continued for six months or until toxicity or progression occurs. CD33-CAR-T cells are administered intravenously at a dose of 5×10$^6$ cells/kg of patient body weight in a single bolus dose 30 days after initiation of IRX5183 dosing.

Pharmacokinetics Analyses. Plasma concentrations of IRX5183 are evaluated for the escalation and expansion phases, targeting safe and effective retinoid levels by pharmacokinetics using LCM-MS (liquid chromatography-mass spectroscopy tandem). Targeting peak levels of 1 pM should avoid systemic toxicity, while presumably preserving local BM niche retinoid levels. The plasma concentration of IRX5183 is obtained using a single 2 mL blood sample, pre-dose on day 14. Samples are shipped to, and analyzed by, the designated analytical laboratory.

Pharmacodynamics Analyses. In addition to assessing standard clinical response criteria, BM cellular (normal HSCs and LSCs) concentrations, peripheral blood and bone marrow blast counts, markers of differentiation, apoptosis, and clonogenic growth are determined. A bone marrow aspirate and biopsy are obtained at baseline, on day 14, and at the end each of the first 4 cycles of therapy. Differentiation is assessed using flow cytometry, comparing expression of differentiation markers on CD45 positive cells and ALDHint LSCs on day 14 marrow versus baseline. FISH analysis is also conducted after each cycle for patients with baseline abnormalities to determine if leukemic clone still present on day 14.

Expected Outcomes

Patients receiving RARα agonist+CD33-CAR-T therapy are monitored for response criteria based on hematological parameters including complete blood counts and percentage of leukemia blasts in the peripheral blood and in the bone marrow. Patients with improved neutrophil count, decreased transfusion requirements of red blood cells and platelets together with decreased percentage of blasts in the bone marrow and induction of differentiation and apoptosis of these malignant blasts are deemed responsive to therapy. Quality of life parameters such as pain, performance status and participation in activity of daily living and instrumental activities of daily living are assessed to evaluate the impact of this therapy on study patients. Use of this RARα agonist+ CD33-CAR-T therapy is expected to improve hematological and quality of life parameters in patients with AML. In addition, the use of a RARα agonist which is CYP26 resistant in combination with CAR-T therapy may result in differentiation and thus elimination of minimal residual disease in the bone marrow of these patients.

Example 8

Clinical Study of IRX5183+CAR-Modified Immune Cells in Multiple Myeloma

Multiple myeloma (MM) is a form of blood cancer that occurs when white blood cells known as plasma cells, which are typically found in the bone marrow, grow out of control and develop into tumors. Approximately 30,000 new cases of multiple myeloma will be diagnosed this year in the U.S. There are few known risk factors for developing this disease and it may not cause signs or symptoms that would lead to a diagnosis until it has advanced to the kidneys and other organs.

B-cell maturation antigen (BCMA) is expressed on all plasma cells, including cancerous plasma cells in MM. Autologous BCMA-CAR-T cells, and their use in MM are disclosed in Ali et al. (Ali SA et al. Blood 128:1688-1700, 2016)..

Inclusion Criteria:
Patients must have histologically confirmed MM by a pathologist, with MM cells expressing BCMA, previously treated with 2+ prior lines of therapy including an IMiD and a PI, either with refractory, persistent, or progressive disease
Age ≥18 years of age
Creatinine ≤2.0 mg/dL, direct bilirubin ≤2.0 mg/dL, AST and ALT ≤3.0× upper limit of normal (ULN)
Adequate pulmonary function as assessed by ≥92% oxygen saturation on room air by pulse oximetry.

Exclusion Criteria:
Karnofsky performance status <70
Pregnant or lactating women. Women and men of childbearing age should use effective contraception while on this study and continue for 1 year after all treatment is finished
Impaired cardiac function (LVEF <40%) as assessed by ECHO or MUGA scan
Patients with following cardiac conditions will be excluded:
New York Heart Association (NYHA) stage III or IV congestive heart failure
Myocardial infarction ≤6 months prior to enrollment
History of clinically significant ventricular arrhythmia or unexplained syncope, not believed to be vasovagal in nature or due to dehydration
History of severe non-ischemic cardiomyopathy
Patients with HIV or active hepatitis B or hepatitis C infection are ineligible
Patients with any concurrent active malignancies as defined by malignancies requiring any therapy other than expectant observation or hormonal therapy, with the exception of squamous and basal cell carcinoma of skin
Patients with a prior allogeneic transplant ARE eligible UNLESS previously or currently experienced GvHD that required systemic steroids or other systemic lymphotoxic therapy
Patients on systemic steroids (except if solely for adrenal replacement) within two weeks of collection
Active autoimmune disease including connective tissue disease, uveitis, sarcoidosis, inflammatory bowel disease, or multiple sclerosis, or have a history of severe (as judged by the principal investigator) autoimmune disease requiring prolonged immunosuppressive therapy
Prior treatment with gene modified T cells
Prior or active CNS involvement by myeloma (eg leptomeningial disease). Screening for this, for example, by lumbar puncture, is only required if suspicious symptoms or radiographic findings are present
Plasma cell leukemia
Pre-existing (active or severe) neurologic disorders (e.g. pre-existing seizure disorder)
Active uncontrolled acute infections
Any other issue which, in the opinion of the treating physician, would make the patient ineligible for the study Modified T cell infusions are administered 2-7 days following the completion of conditioning chemotherapy (cyclophosphamide and optionally fludarabine). BCMA-CAR-T cells are administered at a dose of 1-10×10$^6$ CAR-T cells/kg.

Conditioning chemotherapy comprises cyclophosphamide at 3000 mg/m$^2$ IV once on day D-7 to D-2 or low intensity cy/flu (cyclophosphamide 300 mg/m$^2$/day×3+ fludarabine 30 mg/m$^2$/day×3) with the last day occurring on day D-7 to D-2.

The study uses two doses of IRX5183 in the range of 15-75 mg/m$^2$/day (this range may be narrowed based on the results of the clinical trial in Example 6) and includes three separate arms; one for patients receiving BCMA-CAR-T cells alone (Group 1) and other for patients receiving both IRX5183 and BCMA-CAR-T cells at IRX5183 dose 1 (Group 2) and IRX5183 dose 2 (Group 3), and each of these two arms will recruit 26 patients.

Group 1 patients are treated with BCMA-CAR-T intravenously at a dose of 1-10×10$^6$ cells/kg of patient body weight in a single bolus dose beginning on D0 after conditioning chemotherapy.

Group 2 and 3 patients are treated with daily IRX5183 for 30 days prior to initiating BCMA-CAR-T cells and continued for six months or until toxicity or progression occurs. The BCMA-CAR-T cells are administered intravenously in a single bolus dose of 1-10×10$^6$ cells/kg of patient body weight.

Expected Outcomes

Patients receiving RARα agonist+BCMA-CAR-T therapy are monitored for response criteria based on duration presence of BCMA-CAR-T cells in the subject, tumor growth, metastases, etc. Quality of life parameters such as pain, performance status and participation in activity of daily living and instrumental activities of daily living are assessed to evaluate the impact of this therapy on study patients. Use of this RARα agonist+BCMA-CAR-T therapy is expected to improve quality of life parameters in patients with BCMA-expressing tumors and prevent disease progression. In addition, the use of a RARα agonist which is CYP26 resistant in combination with BCMA-CAR-T therapy may result in differentiation and thus elimination of minimal residual disease in the bone marrow of these patients.

Example 9

Clinical Study of IRX5183+CAR-Modified Immune Cells in Mesothelin-Expressing Solid Tumors Mesothelin is a 40-KDa cell surface tumor differentiation antigen, which derived from the 69-KDa precursor protein encoded by Mesothelin gene. The normal biological function of mesothelin almost remains unknown. Some studies suggest that mesothelin is the receptor of CA125/MUC16, and the interaction between mesothelin-CA125 mediates cell adhesion and may be a critical point in the metastatic of ovarian cancer. Mesothelin overexpression promotes tumor cell proliferation and regional invasion and is associated with poor prognosis, such as worse recurrence-free survival and overall survival. As a tumor marker, soluble mesothelin in serum plays an important role in diagnosing and monitoring therapeutic effect for patients with malignant pleural mesothelioma (MPM) and ovarian cancer. Mesothelin is expressed at low levels in normal tissues, including pleura, pericardium, peritoneum, tunica vaginalis, but it is overexpressed in various malignancies including MPM, ovarian cancers, pancreatic cancers, and non-small cell lung cancers. Due to the weak expression in normal tissues and strong expression in several cancers, mesothelin is an attractive target for immune-based therapies.

Patients will receive a nonmyeloablative but lymphocyte-depleting preparative regimen followed by IV infusion of autologous anti-mesothelin CAR engineered cells (meso-CAR-T cells; disclosed in disclosed in Adusumilli et al., Sci Transl. Med. 6(261):26ra151, 2014) plus low dose IV aldesleukin.

Peripheral blood monocuclear cells (PBMC) obtained by leukapheresis will be cultured in order to stimulate T cell growth. Transduction is initiated by exposure of approximately 1-5×10$^8$ cells to retroviral supernatant containing the anti-mesothelin CAR. Patients will receive a nonmyeloablative but lymphocyte depleting regimen comprising cyclophosphamide and fludarabine (25 mg/m$^2$/day IVPB daily over 30 min for 5 days and cyclophosphamide 60 mg/kg/day×2 days IV in 250 ml D5W over 1 hr) followed by IV infusion of ex vivo CAR gene-transduced PBMC plus low dose aldesleukin (72,000 IU/kg IV over a period of 15 min approximately every eight hours (+/−1 hour) beginning within 24 hours of cell infusion and continuing for up to 5 days for a maximum of 15 doses).

Eligibility

Patients who are 18 years of age or older must have metastatic or unresectable cancer that expresses mesothelin and the patient has previously received and have been a non-responder to, or recurred after, standard care. Patients may not have contraindications for low dose aldesleukin administration.

Inclusion Criteria:

Metastatic or unresectable measurable cancers that express mesothelin. Epithelial mesotheliomas and pancreatic cancers do not need to be assessed for mesothelin expression since all of these tumors have been shown to express mesothelin. Other metastatic or unresectable cancers must be shown to express mesothelin as assessed by RT-PCR or immunochemistry on tumor tissue. Bi-phasic mesotheliomas must express meothelin on greater than 50% of the cells in the epithelial component.

Patients must have previously received at least one systemic standard care (or effective salvage chemotherapy regimens) for metastatic or unresectable disease, if known to be effective for that disease, and have been either non-responders (progressive disease) or have recurred.

Greater than or equal to 18 years of age and less than or equal to 70 years of age.

Willing to sign a durable power of attorney.

Able to understand and sign the Informed Consent Document.

Clinical performance status of ECOG 0 or 1.

Patients of both genders must be willing to practice birth control from the time of enrollment on this study and for up to four months after treatment.

Serology:
  Seronegative for HIV antibody.
  Seronegative for hepatitis B antigen and seronegative for hepatitis C antibody. If hepatitis C antibody test is positive, then patient must be tested for the presence of antigen by RT-PCR and be HCV RNA negative.

Women of child-bearing potential must have a negative pregnancy test because of the potentially dangerous effects of the treatment on the fetus.

Hematology:
  Absolute neutrophil count greater than 1000/mm$^3$ without the support of filgrastim.
  WBC (>3000/mm$^3$).
  Platelet count greater than 100,000/mm$^3$.
  Hemoglobin greater than 8.0 g/dl.

Chemistry:
  Serum ALT/AST less than or equal to 2.5 times the upper limit of normal.
  Serum creatinine less than or equal to 1.6 mg/dl.
  Total bilirubin less than or equal to 1.5 mg/dl, except in patients with Gilbert's Syndrome who must have a total bilirubin less than 3.0 mg/dl/

More than four weeks must have elapsed since any prior systemic therapy at the time the patient receives the preparative regimen, and patient's toxicities must have recovered to a grade of 1 or less (except for toxicities such as alopecia or vitilago).

Exclusion Criteria:

Patients with sarcomatoid mesothelioma

Women of child-bearing potential who are pregnant or breastfeeding.

Patients with known brain metastases.

Patients receiving full-dose anti-coagulative therapy.

Active systemic infections (e.g., requiring anti-infective treatment), coagulation disorders or any other major medical illness.

Any form of primary immunodeficiency

Concurrent opportunistic infections.

Patients with diabetic retinopathy.

Concurrent systemic steroid therapy.

History of severe immediate hypersensitivity reaction to any of the agents used in this study.

History of coronary revascularization or ischemic conditions.

Documented LVEF of less than or equal to 45% tested in patients with:
  Clinically significant atrial and/or ventricular arrhythmias including but not limited to atrial fibrillation, ventricular tachycardia, second or third degree hear block, chest pain, or ischemic heart disease.
  Age greater than or equal to 60 years old.

Documented FEV1 less than or equal to 50% predicted tested in patients with:
  A prolonged history of cigarette smoking (20 pk/year of smoking within the past 2 years).

Symptoms of respiratory dysfunction.

Patients who are receiving any other investigational agents.

Conditioning chemotherapy comprises cyclophosphamide at 3000 mg/m² IV once on day D-7 to D-2 or low intensity cy/flu (cyclophosphamide 300 mg/m²/day×3+fludarabine 30 mg/m²/day×3) with the last day occurring on day D-7 to D-2.

The study uses two doses of IRX5183 in the range of 15-75 mg/m²/day (this range may be narrowed based on the results of the clinical trial in Example 6) and includes three separate arms; one for patients receiving meso-CAR-T cells alone (Group 1) and other for patients receiving both IRX5183 and meso-CAR-T cells at IRX5183 dose 1 (Group 2) and IRX5183 dose 2 (Group 3), and each of these two arms will recruit 26 patients.

Group 1 patients are treated with meso-CAR-T intravenously at a dose of 1-10×10⁶ cells/kg of patient body weight in a single bolus dose beginning on D0 after conditioning chemotherapy.

Group 2 and 3 patients are treated with daily IRX5183 for 30 days prior to initiating meso-CAR-T cells and continued for six months or until toxicity or progression occurs. The meso-CAR-T cells are administered intravenously in a single bolus dose of 1-10×10⁶ cells/kg of patient body weight.

Expected Outcomes

Patients receiving RARα agonist+meso-CAR-T therapy are monitored for response criteria based on duration presence of meso-CAR-T cells in the subject, tumor growth, metastases, etc. Quality of life parameters such as pain, performance status and participation in activity of daily living and instrumental activities of daily living are assessed to evaluate the impact of this therapy on study patients. Use of this RARα agonist+meso-CAR-T therapy is expected to improve quality of life parameters in patients with meso-expressing tumors and prevent disease progression. In addition, the use of a RARα agonist which is CYP26 resistant in combination with meso-CAR-T therapy may result in differentiation and thus elimination of minimal residual disease in the bone marrow of these patients.

Example 10

Clinical Study of IRX5183 +CAR-Modified Immune Cells+Targeted Immunotherapy in Lung Cancer Inclusion criteria and experimental design will be substantially as in Example 9 as follows:

| | |
|---|---|
| Group 1 | meso-CAR-T |
| Group 2 | IRX5183 (optimal dose established in Example 9) + meso-CAR-T |
| Group 3 | meso-CAR-T + PD-1 inhibition |
| Group 4 | IRX5193 + meso-CAR-T + PD-1 inhibition |

Dosing, concomitant medications, and evaluation of outcome will be as in Example 9.

Example 11

Use of IRX5183 in the Manufacture of CAR-Modified T Cells

Autologous T lymphocytes are purified from the peripheral blood of the patient and cultured with feeder cells (such as autologous antigen-presenting cells) and growth factors, such as IL-2.

During the activation process, the T cells are incubated with the viral vector encoding the CAR, and, after several days, the vector is washed out of the culture by dilution and/or medium exchange. The viral vector uses viral machinery to attach to the patient cells, and, upon entry into the cells, the vector introduces genetic material in the form of RNA. In the case of CAR T cell therapy, this genetic material encodes the CAR. The RNA is reverse-transcribed into DNA and permanently integrates into the genome of the patient cells; therefore, CAR expression is maintained as the cells divide and are grown to large numbers in the bioreactor. The CAR is then transcribed and translated by the patient cells, and the CAR is expressed on the cell surface. Lentiviral vectors, which have a safer integration site profile than gammaretroviral vectors are commonly used in clinical trials of CAR T cell therapies.

The transduced cells are then cultured to the desired numbers for multiple rounds of CAR-T therapy. The culture cells can be cryopreserved for future use.

RARα agonists are included in the culture before and/or after transduction with the viral vector to facilitate growth and maintenance of the CAR phenotypes Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of potentiating chimeric antigen receptor-modified immune cells (CAR-MIC) cancer immunotherapy comprising administering at least one differentiating retinoic acid receptor (RAR) active agent, wherein the differentiating RAR active agent is a RARα agonist, to a cancer patient who is receiving, has received, or is scheduled to receive, CAR-MIC, wherein the RARα agonist is a CYP26 metabolism-resistant, RARα selective agonist having a structure of general formula (I)

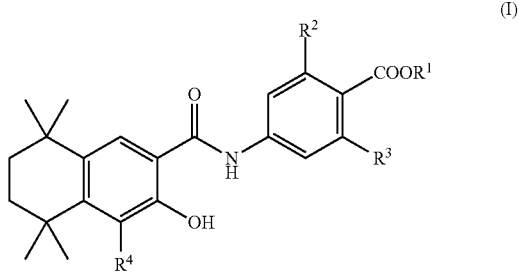

wherein $R^1$ is H or $C_{1-6}$ alky, $R^2$ and $R^3$ are independently H or F, and $R^4$ is a halogen;
wherein the RARα agonist is administered daily.

2. A method of cancer immunotherapy comprising administering to a subject in need thereof CAR-MIC and at least one differentiating RAR active agent, wherein the differentiating RAR active agent is a RARα agonist, wherein the RARα agonist is a CYP26 metabolism-resistant, RARα selective agonist having a structure of general formula (I)

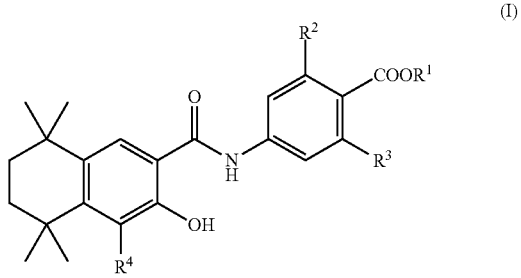

wherein $R^1$ is H or $C_{1-6}$ alky, $R^2$ and $R^3$ are independently H or F, and $R^4$ is a halogen;
wherein the RARα agonist is administered daily.

3. A method of decreasing toxicity of CAR-modified immune cells comprising administering to a subject in need thereof at least one RARα agonist in combination with the CAR-modified immune cells such that as a result of the combination, a lower dose of CAR-modified immune cells is administered but the efficacy is not decreased, as compared to administering the CAR-modified immune cells alone, wherein the RARα agonist is a CYP26 metabolism-resistant, RARα selective agonist having a structure of general formula (I)

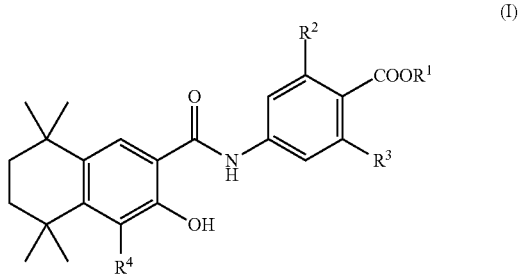

wherein $R^1$ is H or $C_{1-6}$ alky, $R^2$ and $R^3$ are independently H or F, and $R^4$ is a halogen;
wherein the RARα agonist is administered daily.

4. The method of claim 1, wherein the RARα agonist is administered orally.

5. The method of claim 1, wherein the patient is pre-treated with RARα agonist for at least 1 day prior to administration of the CAR-MIC.

6. The method of claim 5, comprising multiple cycles of treatment with the RARα agonist and the CAR-MIC.

7. The method of claim 6, wherein cycles of treatment are continued until a durable complete response is achieved.

8. The method of claim 1, wherein cycles of treatment are continued as long as there is stable disease or the cancer does not progress.

9. The method of claim 2, wherein the RARα agonist is administered orally.

10. The method of claim 2, wherein the patient is pre-treated with RARα agonist for at least 1 day prior to administration of the CAR-MIC.

11. The method of claim 10, comprising multiple cycles of treatment with the RARα agonist and the CAR-MIC.

12. The method of claim 11, wherein cycles of treatment are continued until a durable complete response is achieved.

13. The method of claim 11, wherein cycles of treatment are continued as long as there is stable disease or the cancer does not progress.

14. The method of claim 3, wherein the RARα agonist is administered orally.

15. The method of claim 3, wherein the patient is pre-treated with RARα agonist for at least 1 day prior to administration of the CAR-MIC.

16. The method of claim 15, comprising multiple cycles of treatment with the RARα agonist and the CAR-MIC.

17. The method of claim 16, wherein cycles of treatment are continued until a durable complete response is achieved, or as long as there is stable disease or the cancer does not progress.

* * * * *